United States Patent
Wright et al.

(10) Patent No.: US 9,267,893 B2
(45) Date of Patent: Feb. 23, 2016

(54) TRIPLE SUM FREQUENCY COHERENT MULTIDIMENSIONAL IMAGING

(71) Applicant: Wisconsin Alumni Research Foundation, Madison, WI (US)

(72) Inventors: John Curtis Wright, Oregon, WI (US); Erin Selene Boyle, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/499,741

(22) Filed: Sep. 29, 2014

(65) Prior Publication Data

US 2015/0092190 A1  Apr. 2, 2015

Related U.S. Application Data

(60) Provisional application No. 61/885,069, filed on Oct. 1, 2013.

(51) Int. Cl.
   *G01J 3/44*   (2006.01)
   *G01N 21/65*  (2006.01)
   *G01J 3/02*   (2006.01)

(52) U.S. Cl.
   CPC . *G01N 21/65* (2013.01); *G01J 3/02* (2013.01); *G01J 3/44* (2013.01); *G01N 2201/0697* (2013.01); *G01N 2201/06113* (2013.01)

(58) Field of Classification Search
   CPC .... H01J 37/26; H01J 37/32935; G01N 21/63; G01N 21/64; G01N 21/65; G01N 21/658; G01N 21/68; G01N 2015/1037; G01N 2021/656; G01J 3/02; G01J 3/44
   USPC ............................................. 356/72–73, 301
   See application file for complete search history.

(56) References Cited

U.S. PATENT DOCUMENTS

| | | | |
|---|---|---|---|
| 7,092,086 B2 | 8/2006 | Knebel | |
| 2008/0012850 A1* | 1/2008 | Keating, III | .................. 345/419 |

FOREIGN PATENT DOCUMENTS

WO    WO 9107651    5/1991

OTHER PUBLICATIONS

Boyle et al., Fully Coherent Trile Sum Frequency Spectroscopy of a Benzene Fermi Resonance, The Journal of Physical Chemistry A, vol. 117, Jun. 17, 2013, pp. 5578-5588.

(Continued)

*Primary Examiner* — Abdullahi Nur
(74) *Attorney, Agent, or Firm* — Bell & Manning, LLC

(57) ABSTRACT

Methods of obtaining a multidimensional image of a sample are provided comprising (a) directing a first coherent light pulse having a first frequency $\omega_1$ and a first wave vector $k_1$ at a first location in the sample, (b) directing a second coherent light pulse having a second frequency $\omega_2$ and a second wave vector $k_2$ at the first location, (c) directing a third coherent light pulse having a third frequency $\omega_3$ and a third wave vector $k_3$ at the first location and (d) detecting a coherent output signal having a fourth frequency $\omega_4$ and a fourth wave vector $k_4$. At least two, but optionally all three, of the coherent light pulses each excite a different transition to a discrete quantum state (e.g., transitions to vibrational states or to electronic states) of a molecule or molecular functionality in the sample. Steps (a)-(d) are repeated at a sufficient number of other locations in the sample to provide the multidimensional image.

20 Claims, 21 Drawing Sheets

(56) References Cited

OTHER PUBLICATIONS

Cheng et al., Coherent Anti-Stokes Raman Scattering Microscopy: Instrumentation, Theory, and Applications, J. Phys. Chem. B, vol. 108, Dec. 25, 2003, pp. 827-840.

Denk et al., Two-Photon Laser Scanning Fluorescence Microscopy, Science, vol. 248, Apr. 6, 1990.

Potma et al., Heterodyne coherent anti-Stokes Raman scattering (CARS) imaging, Optics Letters, vol. 31, No. 2, Jan. 15, 2006, pp. 241-243.

Boyle et al., Fully Coherent Hybrid Raman-IR Multidimensional Spectroscopies, Poster, Society for Applied SPectroscopy, SciX, Milwaukee, WI, Sep. 29, 2013.

M. Cho, Theroretical description of two-dimensional vibrational spectroscopy by infrared-infrared-visible sum frequency generation, Physcial Review A, vol. 61, Jan. 2000, pp. 023406-1-023406-12.

M. Cho, Triply resonant infrared-infrared-visible sum frequency generation: Three-dimensional vibronic spectroscopy for the investigation of vibrational and vibronic couplings, Journal of Chemical Physics, vol. 112, No. 20, May 22, 2000, pp. 9002-9014.

M. Cho, Two-dimensional vibrational spectroscopy, VII, Investigation of the vibronic and vibrational couplings by using novel triply resonant two-dimensional vibrational spectroscopies, Journal of Chemical Physics, vol. 113, No. 18, Nov. 8, 2000, pp. 7746-7755.

Bonn et al., Novel Surface Vibrational Spectroscopy: Infrarad-Infrared-Visible Sum-Frequency Generation, Physical Review Letters, vol. 86, No. 8, Feb. 19, 2001, pp. 1566-1569.

M. Cho, Lateral Interactions between adsorbed molecules: Investigations of CO on Ru(001) using nonlinear surface vibrational spectroscopies, Physical Review B, vol. 65, May 23, 2002, pp. 205423-1-205423-10.

Hess et al., Doubly vibrationally resonant spectroscopy of CO on Ru(001), Surface Science, vol. 502-503, 2002, pp. 123-128.

\* cited by examiner

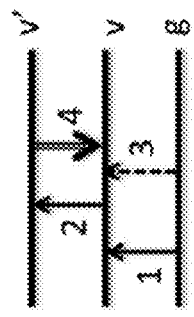
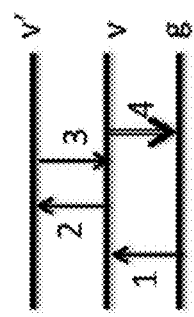
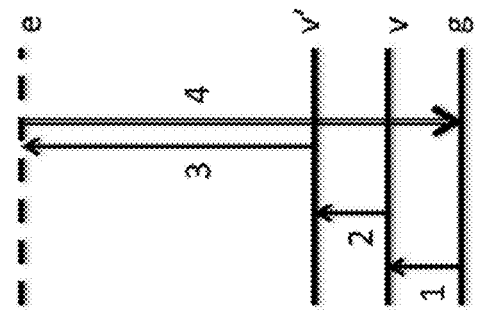
FIG. 1A  FIG. 1B  FIG. 1C
FIG. 1D  FIG. 1E  FIG. 1F

TRIPLE SUM FREQUENCY COHERENT MULTIDIMENSIONAL IMAGING

CROSS-REFERENCE TO RELATED APPLICATIONS

The present application claims priority to U.S. Provisional Patent Application No. 61/885,069 that was filed Oct. 1, 2013, the entire content of which is hereby incorporated by reference.

REFERENCE TO GOVERNMENT RIGHTS

This invention was made with government support under 1057896 awarded by the National Science Foundation. The government has certain rights in the invention.

BACKGROUND

The study of molecular properties in complex chemical and biological samples requires sufficient spatial resolution as well as chemical selectivity. To achieve this, certain spectroscopic techniques have been combined with microscopy in order to investigate the properties of molecules in chemical and biological samples, including live cells. For example, chemically selective three-dimensional imaging of samples has been accomplished using two-photon fluorescence microscopy. In two-photon fluorescence microscopy, fluorophore labeled samples are imaged on a laser scanning microscope by a tightly focused femtosecond pulsed laser having a wavelength in the near-infrared region. However, photobleaching and chemical perturbations inherent in fluorophore labeling are limitations of the technique.

As another example, chemically selective three-dimensional imaging of samples has been accomplished used multiphoton vibrational microscopy based on coherent anti-Stokes Raman scattering (CARS). In CARS, a pump field, a Stokes field and a probe field interact with a sample to generate an anti-Stokes field at the frequency $\omega_{as}=2\omega_p-\omega_s$ and wave vector $k_{as}=2k_p-k_s$. In CARS microscopy, samples are imaged on a laser scanning microscope by a tightly focused pump laser pulse and Stokes laser pulse. (The pump field and probe field are generally derived from the same laser pulse.) Although CARS microscopy avoids the photobleaching problem and is a label-free method, the drawbacks of the technique include an intrinsically weak anti-Stokes signal and significant nonresonant background interference, both of which limit image contrast and spectral selectivity.

SUMMARY

Provided are methods for obtaining multidimensional images of samples and apparatuses for carrying out the methods.

In one aspect, a method of obtaining a multidimensional image of a sample is provided comprising directing a first coherent light pulse having a first frequency $\omega_1$ and a first wave vector $k_1$ at a first location in a sample, directing a second coherent light pulse having a second frequency $\omega_2$ and a second wave vector $k_2$ at the first location, directing a third coherent light pulse having a third frequency $\omega_3$ and a third wave vector $k_3$ at the first location and detecting a coherent output signal having a fourth frequency $\omega_4$ and a fourth wave vector $k_4$ from the first location, wherein $\omega_4=\pm\omega_1\pm\omega_2\pm\omega_3$ and $k_4=\pm k_1\pm k_2\pm k_3$, wherein at least two of the coherent light pulses each are configured to excite a different transition to a discrete quantum state of a molecule or molecular functionality in the sample and further wherein steps (a)-(d) are repeated at a sufficient number of other locations in the sample to provide the multidimensional image.

In another aspect, a scanning microscope for obtaining a multidimensional image of a sample is provided optics configured to receive coherent light pulses and to direct the coherent light pulses to a first location in the sample. The coherent light pulses comprise a first coherent light pulse having a first frequency $\omega_1$ and a first wave vector $k_1$, a second coherent light pulse having a second frequency $\omega_2$ and a second wave vector $k_2$, and a third coherent light pulse having a third frequency $\omega_3$ and a third wave vector $k_3$, wherein at least two of the coherent light pulses each are configured to excite a different transition to a discrete quantum state of a molecule or molecular functionality in the sample. The scanning microscope further comprises a stage configured to support the sample; and a detector positioned to detect a coherent output signal generated from the first location, the coherent output signal having a fourth frequency $\omega_4$ and a fourth wave vector $k_4$, wherein $\omega_4=\pm\omega_1\pm\omega_2\pm\omega_3$ and $k_4=\pm k_1\pm k_2\pm k_3$. The scanning microscope is further configured to illuminate a sufficient number of other locations in the sample with the three coherent light pulses to provide the multidimensional image.

Other principal features of the disclosed subject matter will become apparent to those skilled in the art upon review of the following drawings, the detailed description, and the appended claims.

BRIEF DESCRIPTION OF THE DRAWINGS

Illustrative embodiments of the disclosed subject matter will hereafter be described with reference to the accompanying drawings.

FIG. 1A depicts the wave-mixing energy level (WMEL) diagrams for Triple Sum Frequency (TSF). FIG. 1B depicts a WMEL diagram for double quantum four-wave mixing (FWM). FIG. 1C depicts a WMEL diagram for double quantum four-wave mixing (FWM). FIG. 1D depicts a WMEL diagram for Doubly Vibrationally Enhanced (DOVE)-Raman. FIG. 1E depicts a WMEL diagram for DOVE-IR. FIG. 1F depicts a WMEL diagram for DOVE-IR. The numbers label the excitation pulse frequencies and have no correlation with their time ordering.

DETAILED DESCRIPTION

Figure 2A:
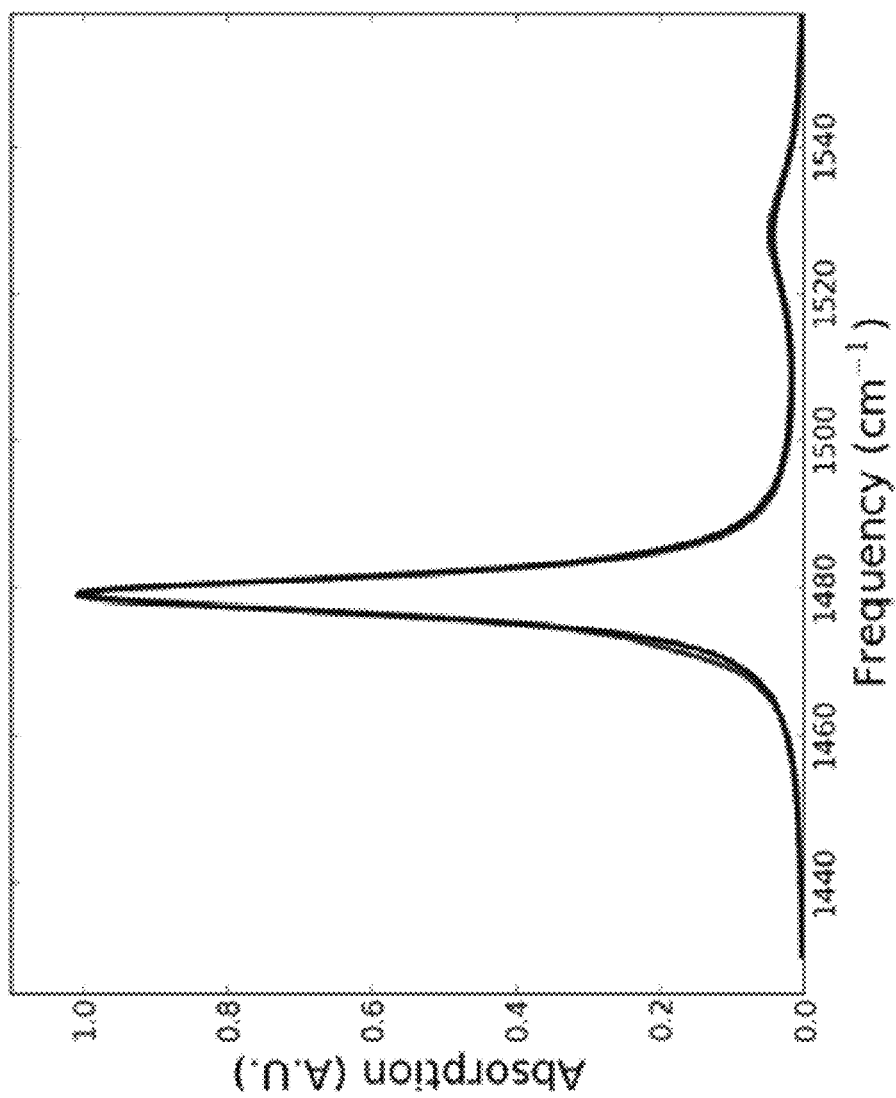
FIG. 2A shows benzene's high-resolution infrared absorption spectrum (provided by Bertie).

Provided are methods for obtaining multidimensional images of samples and apparatuses for carrying out the methods.

The methods involve the use of multiple (e.g., three) coherent pulses of light to excite multiple (e.g., two or three) quantum states of molecules or molecular functionalities present in a sample. Coherent excitation of the multiple quantum states via the interaction of the coherent light pulses with the electric dipoles of the molecules or molecular functionalities generates a coherent output signal. The coherent output signal is greatly enhanced when the coherent excitation pulses are resonant with transitions between quantum states. Multiple locations in a sample (i.e., locations defined by unique sets of x, y, z coordinates) can be illuminated with spatially overlapped coherent excitation pulses and the coherent output signal detected at each location to provide a multidimensional (e.g., 2D or 3D) image of the sample. Multiresonant excitation both enhances the intensity of the coherent output signal and suppresses background (since quantum state transitions are specific to the different molecules or molecular functionalities in the sample). Thus, multidimensional images obtained using the disclosed methods may exhibit improved contrast as compared to images obtained with conventional imaging methods even when the concentration of the excited molecules or molecular functionalities in the sample is very low.

The methods may be used to provide chemically selective, multidimensional images of a variety of types of chemical and biological samples. Such samples will include different molecules or functionalities on molecules (i.e., molecular functionalities, e.g., C—H bonds) having certain vibrational and electronic characteristics. These molecules or molecular functionalities can be identified and studied by using a set of coherent excitation pulses to probe these vibrational and electronic characteristics. The molecules or molecular functionalities referred to herein may be "target" molecules or molecular functionalities in that their existence in a particular sample may be initially unknown. The methods can be used to determine the presence or absence of such molecules/molecular functionalities in the samples. The methods will find applications in a variety of fields including membrane biology, neurobiology, pathology, pharmacology and composite materials.

The disclosed methods employ various coherent multidimensional spectroscopic (CMDS) excitation schemes. The field of coherent multidimensional spectroscopy (CMDS) uses a series of excitation pulses that are bright enough to create time-dependent multiple quantum coherences (MQCs). The MQCs launch new, directional light fields at the frequency differences between the MQC states for the duration of the coherence. The emission occurs only between pairs of states that are coupled. The intensity of the emission informs the observer of coupling between the modes of the system and therefore describes its structure. Dynamics are explored by observing dephasing rates and changes in couplings over time. Because the wave vector for the nonlinear output polarization is the sum of the input wave vectors weighted by the positive or negative phase of interaction, the phase of each field interaction can be defined by observing the output launched in a specific direction. That direction is described by conservation of momentum between the input and output fields. This phase-matching condition helps to define the quantum pathway represented by light emitted in a certain direction.

Vibrational CMDS is divided into two different approaches. Two-dimensional infrared or electronic spectroscopy (2D-IR or 2D-ES) are time domain Four Wave Mixing (FWM) methods where the wide bandwidth of ultrafast excitation pulses excites multiple quantum states and the delay times between pulses map out the frequencies and decay times of the coherences through their temporal interference. Multiresonant CMDS is a frequency domain method where the excitation pulses are long enough to excite individual quantum states but short enough to map out their dynamics. Both methods are capable of using fully coherent pathways where populations are not created. Multiresonant methods access a wider range of quantum states because they only require short-term phase coherence during the nonlinear mixing. This difference removes the constraint imposed by the excitation bandwidth and allows any set of vibrational and electronic states to be probed, regardless of frequency.

In the time domain methods (e.g., 2D-IR and 2D-ES), the experiments generally employ pulses of duration of ~50 fs and bandwidth ~300 cm$^{-1}$. The phase oscillations of each coherence are resolved by heterodyning the output with a local oscillator, scanning the time delays between pulses, and Fourier transforming the signals to the frequency domain. In multiresonant CMDS experiments, pulses are designed to have spectral and temporal width matching the dephasing times of interest in the sample (often ~4 ps, ~20 cm$^{-1}$ for vibrational spectroscopy). With this design, each pulse has the spectral width to excite single modes, and temporally define the sequence of interactions between quantum states. Frequencies are scanned to obtain spectral information and pulses are delayed to map out dynamics. Multiresonant CMDS can use any combination of electronic and vibrational states.

In one embodiment, a method of obtaining a multidimensional image of a sample comprises (a) directing a first coherent light pulse having a first frequency $\omega_1$ and a first wave vector $k_1$ at a first location in a sample, (b) directing a second coherent light pulse having a second frequency $\omega_2$ and a second wave vector $k_2$ at the first location, (c) directing a third coherent light pulse having a third frequency $\omega_3$ and a third wave vector $k_3$ at the first location and (d) detecting a coherent output signal having a fourth frequency $\omega_4$ and a fourth wave vector $k_4$ from the first location. In the method, at least two of the coherent light pulses each are configured to excite a different transition to a discrete quantum state of a molecule or molecular functionality in the sample. The term "discrete" is used to distinguish the quantum state from a virtual quantum state. In the method, steps (a)-(d) are repeated at a sufficient number of other locations in the sample to provide the multidimensional image.

The transitions excited by at least two of the coherent light pulses may be transitions to vibrational quantum states (e.g., a fundamental mode, an overtone, or a combination band) or to electronic quantum states. One of the two coherent light pulses may excite a transition to a vibrational quantum state and the other may excite a transition to a different vibrational quantum state. Alternatively, one of the two coherent light pulses may excite a transition to a vibrational quantum state and the other may excite a transition to an electronic quantum state. The excitations achieved by the two coherent light pulses may be single-quantum excitations or multiple-quantum, e.g., two-quantum excitations.

As discussed above, at least two of the coherent light pulses each excite a different transition to a discrete quantum state of a molecule or molecular functionality in the sample. The remaining coherent light pulse may be configured to excite a transition to a virtual quantum state (e.g., a virtual electronic state), whereby a Raman transition is induced returning the molecule or molecular functionality to a lower energy state (e.g., the ground state). Alternatively, the remaining coherent light pulse may excite a transition to a discrete quantum state (e.g., an electronic quantum state), whereby a "resonance Raman" transition is induced returning the molecule or molecular functionality to a lower energy state. Either Raman transition may be a single-quantum or a multiple-quantum transition. The excitation may be a single-photon excitation.

Figure 14:
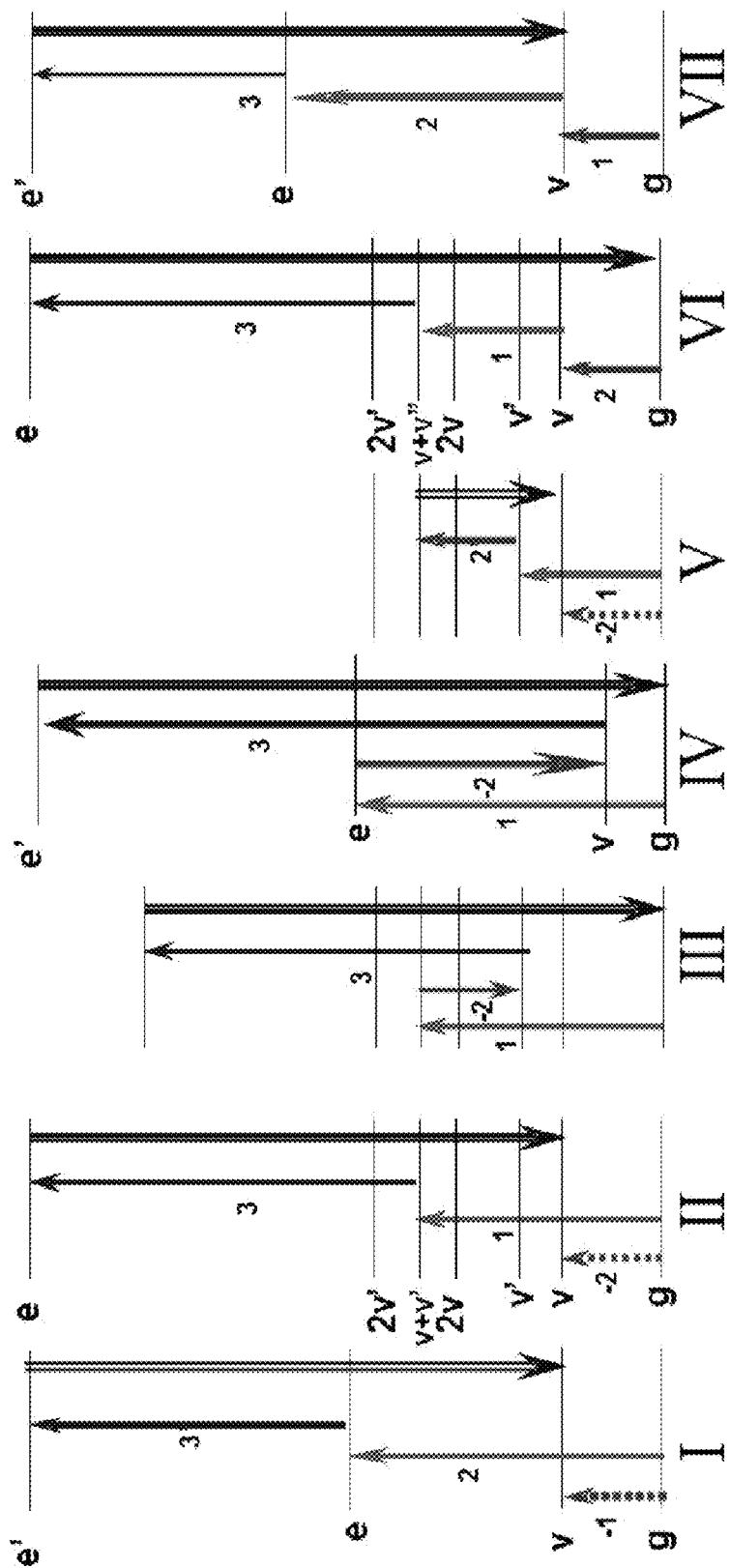
FIG. 14 depicts the wave-mixing energy level (WMEL) diagrams for additional CMDS excitation schemes.

Examples of specific CMDS excitation schemes are shown in FIG. 1 and described in the Examples below. FIG. 14 includes other examples of excitation schemes. Pathways II and III are DOVE-IR and DOVE-Raman pathways (see FIG. 1D-F). Pathway VI is a triply resonant sum frequency (TRSF) pathway. Pathways I, IV, and VII are similar to DOVE-IR, DOVE-Raman, and TRSF, respectively, but substitute a second electronic transition for the combination band transition in the infrared, giving different selectivity. Pathway V is a fully infrared pathway.

The coherent light pulses may be characterized by a number of properties, such as the frequency, $\omega$, of each light pulse. The selected frequency generally depends upon the desired CMDS excitation scheme as well as the molecule or molecular functionality to be imaged. The frequency of a coherent light pulse may be fixed or may be tuned (i.e., scanned) over a range of frequencies. Again, the selected range generally depends upon the desired CMDS excitation scheme as well as the molecule or molecular functionality to be imaged. In order to enhance the coherent output signal, the selected frequency can be that which is resonant with the transition to be excited with the coherent light pulse (or the range of frequencies is selected to encompass the resonant frequency). The frequency of a coherent light pulse may be independently tunable from another coherent light pulse, i.e., the selection of a range of frequencies over which one coherent light pulse is to be tuned does not depend upon the selected frequency of another coherent light pulse or the range of frequencies over which the other coherent light pulse is tuned. Suitable frequencies and ranges of frequencies include those in the infrared region (e.g., from about $10^4$ cm$^{-1}$ to about 10 cm$^{-1}$), those in the visible region (e.g., from about $2.5 \times 10^4$ cm$^{-1}$ to about $10^4$ cm$^{-1}$), and those in the ultraviolet region (e.g., from about $10^6$ cm$^{-1}$ to $2.5 \times 10^4$ cm$^{-1}$) of the electromagnetic spectrum. For multiple coherent light pulses, e.g., a first coherent light pulse having a first frequency $\omega_1$, a second coherent light pulse having a second frequency $\omega_2$, and a third coherent light pulse having a third frequency $\omega_3$, the subscripts are meant only to distinguish individual, independent coherent light pulses from one another. The selected frequency or range of frequencies for one coherent light pulse (e.g., a first coherent light pulse having a first frequency $\omega_1$) may be the same or different as another coherent light pulse (e.g., a second coherent light pulse having a second frequency $\omega_2$).

The coherent light pulses may be characterized by a number of other properties including spectral width and temporal width, which are generally selected based upon the desired CMDS excitation scheme. The coherent light pulses may be characterized by pulse energy, which is generally selected to provide sufficient intensity to ensure nonlinear interactions with certain molecules or molecular functionalities within the sample. The coherent light pulses may be characterized by repetition rate, which is generally selected to provide a desired acquisition speed for the image. Another property characterizing the coherent light pulse is its wave vector, k.

A coherent light pulse may be characterized by the orientation of its propagation axis relative to normal to the plane of the sample. For example, a coherent light pulse may have a propagation axis which is normal to the sample plane. Alternatively, a coherent light pulse may have a propagation axis which forms an angle $\theta$ relative to normal. The coherent light pulses may be configured in a non-collinear beam geometry in which different coherent light pulses are characterized by different propagation axes. (See, e.g., FIGS. 9 and 10.)

The coherent light pulses may be characterized by the time delays between different coherent light pulses. By way of example only, time delays may be defined relative to a first coherent light pulse such that $\tau_{21}=\tau_2-\tau_1$ and $\tau_{31}=\tau_3-\tau_1$. (See, e.g., Example 1.) The time delays determine the order in which the coherent light pulses interact with the sample and in general, any order may be used. Coherent light pulses may be considered to be temporally overlapped when the time delay between the coherent light pulses is substantially zero. The time delay between coherent light pulses may be fixed (e.g., to collect a frequency spectrum with a certain pathway) or may be scanned over a range of time delays (e.g., to learn dynamics).

Various embodiments of the method may be conducted in which the frequencies of the coherent light pulses are fixed or tuned and in which the time delays between different coherent light pulses are fixed or scanned. By way of example only, in some embodiments, the frequencies of each of the coherent light pulses are fixed and the time delays between different coherent light pulses are fixed. Such an embodiment may be useful for obtaining a "chemical map" of a specific known molecule or molecular functionality in a sample. The Examples, below, describe other embodiments of the method.

As discussed above, the coherent light pulses are spatially overlapped at various locations on or within the sample. The coherent light pulses may be configured such that the pulses are substantially fully overlapped in space, i.e., the centers of each spot illuminated by its respective coherent light pulse are substantially coincident. However, the coherent light pulses may be configured such that the pulses are partially spatially overlapped, i.e., the centers of one or more spots illuminated by its respective coherent light pulse are not coincident. A partially spatially overlapped configuration may allow for the spatial region probed by the coherent light pulses to be smaller than the smallest diffraction limited spot size.

As discussed above, the multiple coherent light pulses interact with molecules or molecular functionalities in a sample to generate a nonlinear output polarization, which acts as the source of radiation for a coherent output signal having a specific frequency and wave vector as determined by the CMDS excitation scheme, the phase of interaction and conservation of momentum. In addition, for a particular CMDS excitation scheme, different coherent output signals having different frequencies and wave vectors associated with different quantum pathways may be possible. Particular quantum pathway(s) may be monitored by detecting the coherent output signal(s) in the corresponding phase-matched direction(s). The detection of the desired coherent output signal and discrimination from other possible coherent output signals may be facilitated by placing the detector coincident with the desired phase-matched direction, by using certain beam geometries, and by using apertures to physically block undesired signals. In addition, altering the propagation axes of the coherent light pulses and therefore, the propagation axis of the corresponding coherent output signal allows for different pathways, such as those in FIGS. 1 and 14, to be phase-matched. Interrogating different pathways can provide different information about the chemical makeup of the sample.

In some embodiments, a method of obtaining a multidimensional image of a sample comprises (a) directing a first coherent light pulse having a first frequency $\omega_1$ and a first wave vector $k_1$ at a first location in a sample, (b) directing a second coherent light pulse having a second frequency $\omega_2$ and a second wave vector $k_2$ at the first location, (c) directing a third coherent light pulse having a third frequency $\omega_3$ and a third wave vector $k_3$ at the first location and (d) detecting a coherent output signal having a fourth frequency $\omega_4$ and a fourth wave vector $k_4$ from the first location, wherein $\omega_4=\pm\omega_1\pm\omega_2\pm\omega_3$ and $k_4=\pm k_1\pm k_2\pm k_3$. In the method, two of the coherent light pulses are each configured to excite a different transition to a discrete quantum state (e.g., different vibrational quantum states or a vibrational quantum state and an electronic quantum state) of a molecule or molecular functionality in the sample. The remaining coherent light pulse may be configured to excite a transition to a virtual quantum state (e.g., a virtual electronic state), whereby a Raman transition is induced returning the molecule or molecular functionality to a lower energy state (e.g., the ground state). Alternatively, the remaining coherent light pulse may be configured to excite a transition to a discrete quantum state (e.g., an electronic quantum state), whereby a "resonance Raman" transition is induced to return the molecule or molecular functionality to a lower energy state. In the method, steps (a)-(d) are repeated at a sufficient number of other locations in the sample to provide the multidimensional image.

In some embodiments, a method of obtaining a multidimensional image of a sample comprises (a) directing a first coherent light pulse having a first frequency $\omega_1$ and a first wave vector $k_1$ at a first location in a sample, (b) directing a second coherent light pulse having a second frequency $\omega_2$ and a second wave vector $k_2$ at the first location, (c) directing a third coherent light pulse having a third frequency $\omega_3$ and a third wave vector $k_3$ at the first location and (d) detecting a coherent output signal having a fourth frequency $\omega_4$ and a fourth wave vector $k_4$ from the first location, wherein $\omega_4=\omega_1+\omega_2+\omega_3$ and $k_4=k_1+k_2+k_3$. In the method, steps (a)-(d) are repeated at a sufficient number of other locations in the sample to provide the multidimensional image. As discussed above, two of the coherent light pulses may each be configured to excite a different transition to a discrete quantum state (e.g., different vibrational quantum states or a vibrational quantum state and an electronic quantum state) of a molecule or molecular functionality in the sample. The remaining coherent light pulse may be configured to excite a transition to a virtual quantum state (e.g., a virtual electronic state), whereby a Raman transition is induced returning the molecule or molecular functionality to a lower energy state (e.g., the ground state). Alternatively, the remaining coherent light pulse may be configured to excite a transition to a discrete quantum state (e.g., an electronic quantum state), whereby a "resonance Raman" transition is induced to return the molecule or molecular functionality to a lower energy state. These embodiments may be referred to as triple sum frequency (TSF) schemes (if they involve excitation of two discrete quantum states) or triply resonant sum frequency (TRSF) schemes (if they involve excitation of three discrete quantum states).

In some embodiments, one of the coherent light pulses excites a transition to a vibrational quantum state (e.g., a fundamental mode), one of the coherent light pulses excites a transition to a different vibrational quantum state (e.g., an overtone or combination band), and one of the coherent light pulses excites a transition to a virtual electronic state, whereby a Raman transition is induced returning the molecule or molecular functionality to a lower energy state. In some embodiments, one of the coherent light pulses excites a transition to a vibrational quantum state (e.g., a fundamental mode), one of the coherent light pulses excites a transition to a different vibrational quantum state (e.g., an overtone or combination band), and one of the coherent light pulses excites a transition to an electronic quantum state, whereby a "resonance Raman" transition is induced returning the molecule or molecular functionality to a lower energy state. In some embodiments, one of the coherent light pulses excites a transition to a vibrational quantum state, one of the coherent light pulses excites a transition to a electronic quantum state, and one of the coherent light pulses excites a transition to a different electronic quantum state, whereby a "resonance Raman" transition is induced returning the molecule or molecular functionality to a lower energy state.

The Examples below further describe methods employing TSF and TRSF excitation schemes.

As discussed above, methods employing TSF or TRSF excitation schemes involve detecting a coherent output signal having a fourth frequency $\omega_4$ and a fourth wave vector $k_4$, wherein $\omega_4=\omega_1+\omega_2+\omega_3$ and $k_4=k_1+k_2+k_3$. Because this quantum pathway cannot be phase matched in systems with normal dispersion, the inventors' findings that the corresponding coherent output signal was not only detectable but also more intense than coherent output signals obtained using other CMDS excitation schemes are unexpected. The inability to achieve phase matching for this pathway means that there is no beam geometry that can prevent the coherent output signal from molecules near the front of the sample from interfering destructively with the coherent output signal from molecules at the opposite end of the sample. However, the inventors found that the gain of this pathway (i.e., the ability for the pathway to generate signal as a function of path length, the distance over which the coherent light pulses interact with molecules or molecular functionalities in the sample) was much higher than expected. Moreover, the inventors have found that the path length is an important parameter that affects the intensity of the coherent output signal in the $k_4=k_1+k_2+k_3$ direction. Generally, the path length should be sufficiently large to maximize the gain, but sufficiently small to minimize the problem of the destructive interference of the coherent output signal. The range of suitable path lengths depends upon a number of other parameters, including the particular sample and the particular quantum state transitions to be excited. However, in some embodiments, the path length is in the range of from about 1 µm to about 200 µm. This includes embodiments in which the path length is in the range of from about 1 µm to about 150 µm, from about 1 µm to about 100 µm or from about 1 µm to about 50 µm.

The methods may be carried out on a variety of scanning microscopes, including confocal scanning microscopes. In one embodiment, the scanning microscope comprises optics configured to receive coherent light pulses from light sources and to direct the pulses into a sample. These optics may include optics configured to direct the coherent light pulses along desired propagation axes to achieve a desired beam geometry (i.e., a collinear beam geometry or a non-collinear beam geometry) and optics (e.g., an objective lens) configured to focus the coherent light pulses into the sample. The scanning microscope also comprises a stage configured to support the sample and a detector (e.g., a photomultiplier tube) configured to receive and to detect a coherent output signal generated from the sample.

The scanning microscope may comprise a variety of other components known to be useful for scanning microscopy. The scanning microscope may comprise the light sources (and associated optics) configured to generate coherent light pulses having certain of the characteristics described herein (e.g., frequency, spectral width, temporal width, pulse energy). The scanning microscope may comprise optics configured to adjust the time delay between the coherent light pulses. The scanning microscope may comprise optics configured to receive light generated from the sample or passing through the sample and to direct the light towards a detector, including optics configured to focus or collimate the light. The scanning microscope may comprise an aperture configured to receive light generated from the sample or passing through the sample and to block undesired light (e.g., certain coherent excitation pulses or undesired coherent output signals). This or another aperture may also be configured to block light generated from regions within the sample which are outside the focus region, although such apertures may not be necessary due to the improvement in contrast obtained via the use of multiresonant excitation. The scanning microscope may comprise optical filters configured to receive light generated from the sample or passing through the sample and to block undesired light (e.g., certain coherent excitation pulses). Monochromators may also be used for this purpose.

Obtaining a multidimensional image of the sample using the scanning microscope requires illuminating multiple locations in a sample with spatially overlapped coherent excitation pulses and detecting the coherent output signal generated at each location. This may be achieved by scanning the coherent excitation pulses relative to the sample, e.g., via scanning optics in the scanning microscope, or by scanning the sample relative to the coherent excitation pulses, e.g., via a scanning stage. In the former case, the scanning optics typically control the x and y position of the coherent excitation pulses relative to the sample. The z position may be controlled by adjusting the position of the objective lens relative to the sample. The scanning optics for scanning the coherent excitation pulses relative to the sample may include galvano scanners, e.g., such as those available on the Nikon A1 MP confocal microscope available from Nikon Instruments, Inc. The spatial resolution that is possible in the scanning microscope is determined by the diffraction limited spot size of the highest frequency of the coherent excitation pulses and the coherent output signal.

Figure 16:
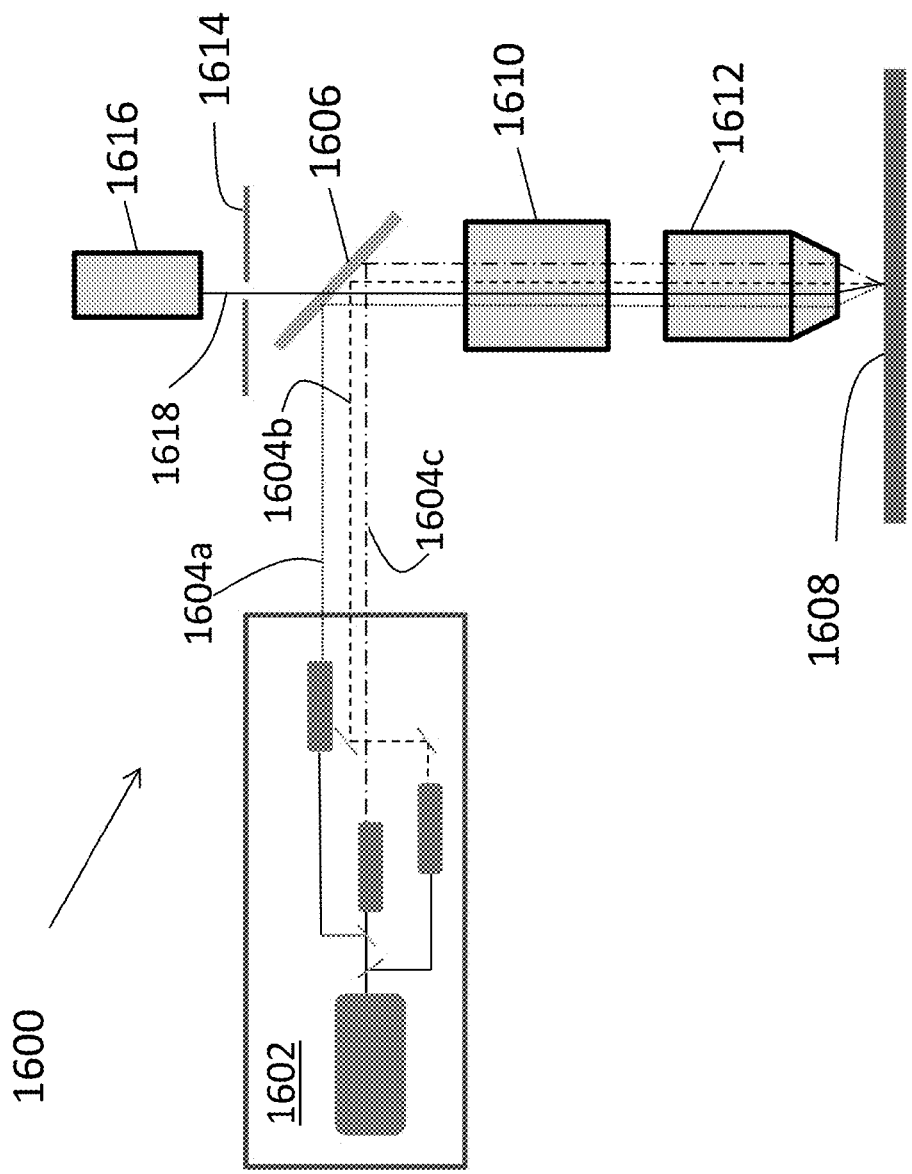
FIG. 16 depicts a schematic of a scanning microscope for carrying out the disclosed methods for obtaining multidimensional images of samples.

FIG. 16 shows an exemplary embodiment of a scanning microscope 1600 for carrying out any of the disclosed methods. The scanning microscope 1600 may include a coherent multidimensional spectroscopy (CMDS) laser system 1602 which may include the light sources and associated optics configured to generate coherent light pulses 1604 *a-c* having certain of the characteristics described herein. The scanning microscope 1600 may include a dichroic mirror 1606 configured to direct the coherent light pulses towards a sample on a stage 1608 configured to support the sample. The scanning microscope 1600 may include a laser scanning system 1610 which may include scanning optics for scanning the coherent excitation pulses 1604 *a-c* relative to the sample. The scanning microscope 1600 may include a microscope objective 1612 configured to focus the coherent light pulses 1604 *a-c* into the sample. The scanning microscope 1600 may include a pinhole aperture 1614 configured to receive light generated from the sample or passing through the sample and to block undesired light from impinging upon a photomultiplier tube 1616 configured to receive and to detect a coherent output signal 1618 generated from the sample.

The scanning microscope may further comprise components for controlling certain operations of the scanning microscope, e.g., the illumination of different locations within the sample with the coherent excitation pulses or the reconstruction of a multidimensional image from the coherent output signal detected at the different locations. For example, the scanning microscope may further comprise a processor and a computer-readable medium operably coupled to the processor, the computer-readable medium having computer-readable instructions stored thereon that, when executed by the processor cause the scanning microscope to perform certain operations, e.g., operations related to illuminating a particular location within the sample or to reconstructing an image from detected signals. For example, the scanning microscope may further comprise a processor and a non-transitory computer-readable medium operably coupled to the processor, the computer-readable medium having computer-readable instructions stored thereon that, when executed by the processor cause the scanning microscope to illuminate a first location within the sample with a first coherent light pulse having a first frequency $\omega_1$ and a first wave vector $k_1$, a second coherent light pulse having a second frequency $\omega_2$ and a second wave vector $k_2$, and a third coherent light pulse having a third frequency $\omega_3$ and a third wave vector $k_3$ to generate a first coherent output signal characterized by $\omega_4=\pm\omega_1\pm\omega_2\pm\omega_3$ and $k_4=\pm k_1\pm k_2\pm k_3$; receive the first coherent output signal from the detector; illuminate multiple other locations within the sample with the three coherent light pulses to generate multiple other coherent output signals, each characterized by $\omega_4=\pm\omega_1\pm\omega_2\pm\omega_3$ and $k_4=\pm k_1\pm k_2\pm k_3$; reconstruct a multidimensional image from the received coherent output signals; and output the multidimensional image.

The methods will be understood more readily by reference to the following examples, which are provided by way of illustration and are not intended to be limiting.

EXAMPLES

Example 1

Fully Coherent Triple Sum Frequency Spectroscopy of a Benzene Fermi Resonance

This example is derived from Boyle et al. Fully Coherent Triple Sum Frequency Spectroscopy of a Benzene Fermi Resonance, *J. Phys. Chem. A* 2013, 117, 5578-5588 and accompanying supporting information, each which is hereby incorporated by reference in its entirety.

Introduction

The two dominant forms of multiresonant vibrational CMDS are Doubly Vibrationally Enhanced (DOVE) CMDS and Triply Vibrationally Enhanced (TRIVE) CMDS. Each approach uses three excitation pulses and the phase matching condition $\vec{K}_1-\vec{K}_2+\vec{K}_3$, where the subscripts designate the frequencies. DOVE CMDS uses two infrared pulses to excite vibrational states and a higher frequency third pulse to excite a Raman transition between the vibrational states. One of the infrared transitions is a two-quantum transition directly to an overtone or combination band. The output at $\omega_1-\omega_2+\omega_3$ appears in the visible or ultraviolet and is spectrally distinct from the excitation frequencies. TRIVE CMDS uses three infrared pulses to excite vibrational states and the output appears in the infrared. The Klug group has applied DOVE to benzene in a comparable spectral region to that presented in this example, offering an interesting comparison of the two methods. (See, Donaldson, P. M.; Guo, R.; Fournier, F.; Gardner, E. M.; Barter, L. M. C.; Barnett, C. J.; Gould, I. R.; Klug, D. R.; Palmer, D. J.; Willison, K. R. Direct Identification and Decongestion of Fermi Resonances by Control of Pulse Time Ordering in Two-dimensional IR Spectroscopy. *J. Chem. Phys.* 2007, 127, 114513.) For a centrosymmetric molecule such as benzene, it turns out that the overtone and combination bands states seen in the two methods are mutually exclusive.

This example reports multiresonant Triple-Sum Frequency (TSF) CMDS with the use of benzene as a model system. It uses the fully additive phase matching pathway $\vec{K}_1+\vec{K}_2+\vec{K}_3$. This pathway is not able to achieve the phase matched condition in systems with normal dispersion, and yet the output signal is even brighter than the comparable DOVE CMDS of benzene. FIG. 1A shows TSF CMDS has only a single coherence pathway involving a simple ladder climbing of states. It is a fully coherent parametric pathway that does not involve any intermediate populations and it returns the system to the ground state. No energy is deposited in the molecular system. Unlike DOVE, the first two transitions are each single-quantum interactions that evolve the system first to fundamental and then to overtone or combination band vibrational coherences. The final excitation creates a Raman transition. The output is spectrally isolated at the sum frequency of the inputs where high-efficiency detectors are available.

Because this ladder-climbing has only a single pathway, spectral interpretation is clear and there cannot be any interference effects between pathways. The fundamental transitions appear along one axis and the overtones and combination bands appear along the other. This separation is similar to double quantum FWM, a fully vibrational technique where anharmonicity can be deduced directly from the frequency of the double quantum axis. However, double quantum FWM includes interference between two pathways with opposite phases that involve the fundamental and an overtone or combination band (FIG. 1B,C). These pathways destructively interfere in the absence of coupling between the states and lead to the disappearance of the peak. The other FWM pathways for 2D-IR and TRIVE also exhibit these same interference effects between parametric pathways that return the system to the ground state and nonparametric pathways that involve overtones or combination bands and leave the system in an excited state. These interference effects are absent in TSF CMDS where there is a single pathway and all peaks share positive phase. Enhancement in this case can be due to electrical as well as mechanical anharmonicity. Finally, in TSF CMDS there can be no generation of a population state and the pathway is therefore fully coherent. This technique therefore offers an interesting probe of coherence transfer because this is the only process that would create a new output frequency.

Experimental

Data were collected on a modified version of a previously described laser system. (See, Block, S. B.; Yurs, L. A.; Pakoulev, A. V.; Selinsky, R. S.; Jin, S.; Wright, J. C. Multiresonant Multidimensional Spectroscopy of Surface-Trapped Excitons in PbSe Quantum Dots. *J. Phys. Chem. Lett.* 2012, 3, 2707-2712.) Briefly, an 80 MHz mode-locked Ti:Sapphire SpectraPhysics Tsunami femtosecond oscillator seeded a regenerative amplifier, pumped by a 1 kHz, 9 W Nd:YLF Empower. The 800 nm, 1.0-1.6 ps, 12 cm$^{-1}$ amplifier output was split to pump two independently tunable optical parametric amplifiers (OPAs) with frequencies $\omega_1$ and $\omega_2$ in the mid-IR, 20-25 cm$^{-1}$ fwhm Gaussian profiles, ~0.8-1 ps durations, and 1-1.5 μJ pulse energies. A third excitation beam ($\omega_3$) with a 2 μJ/pulse of 800 nm light was created by further splitting the amplifier output. The $\omega_2$ and $\omega_3$ time delays were changed relative to the $\omega_1$ beam by times $\tau_{21}$ and $\tau_{31}$. Note that in this notation, numerical indices refer to the beamline and not the quantum state or time ordering. This notation allows for two-dimensional scans to be described self-consistently, not only in frequency space but in delay space as well. In the former, a fixed $\tau_{21}$ and $\tau_{31}$ will define the pathway that is being probed. In the latter, frequencies are fixed and relative time delays are varied over positive and negative values in order to probe all possible time ordered pathways. For TSF, these two-dimensional delay scans map out each of the coherence dephasing rates.

All fields were focused into the sample by either a 50 or 100 mm focal length off-axis parabolic mirror. The experimental phase-matching geometry placed the visible beam normal to the sample plane and the infrared fields at ±10°. The wave vector for the nonlinear output polarization is the sum of the excitation pulse wave vectors, $\vec{k}_4 = \vec{k}_1 + \vec{k}_2 + \vec{k}_3$, so the desired TSF output is therefore collinear to the visible field as the momenta of the IR fields will cancel when the frequencies are similar. It should be noted that the TSF pathways $2\vec{k}_1 + \vec{k}_3$ and $2\vec{k}_2 + \vec{k}_3$ result in strong FWM as well, and that these outputs occur at ~2-3° to the visible beam and are spatially removed. Spectral discrimination of the signal from the visible input was achieved by a combination of high optical density 600 nm long-pass and 800 nm notch filters. A McPherson Model 218A monochromator measured the TSF signal for experiments that resolved the output frequency with a resolution of 11 cm$^{-1}$. The OPAs and laser table are purged with dry air, maintaining a relative humidity of ~2%.

The tuning of $\omega_1$ and $\omega_2$ over 200 cm$^{-1}$ changed the delay times by ~0.3 ps, largely as a result of the path-length change in the AgGaS$_2$ DFG crystal. It was found that inducing either two-photon fluorescence or nonresonant TSF signal in a 2 mm ZnSe crystal provided a convenient and very intense output for finding an approximate zero delay time. However, the temporal breadth of the ZnSe signal results in slight variations of zero delay definition from day to day, which can slightly change the relative intensities of benzene's two peaks as well as change the temporal offset in Wigner data.

The sample was neat benzene held between two 150 μm CaF$_2$ windows with a Teflon spacer of path length 15 μm. Infrared spectra of the sample were identical with those obtained with benzene dried by distillation over sodium.

Figure 9:
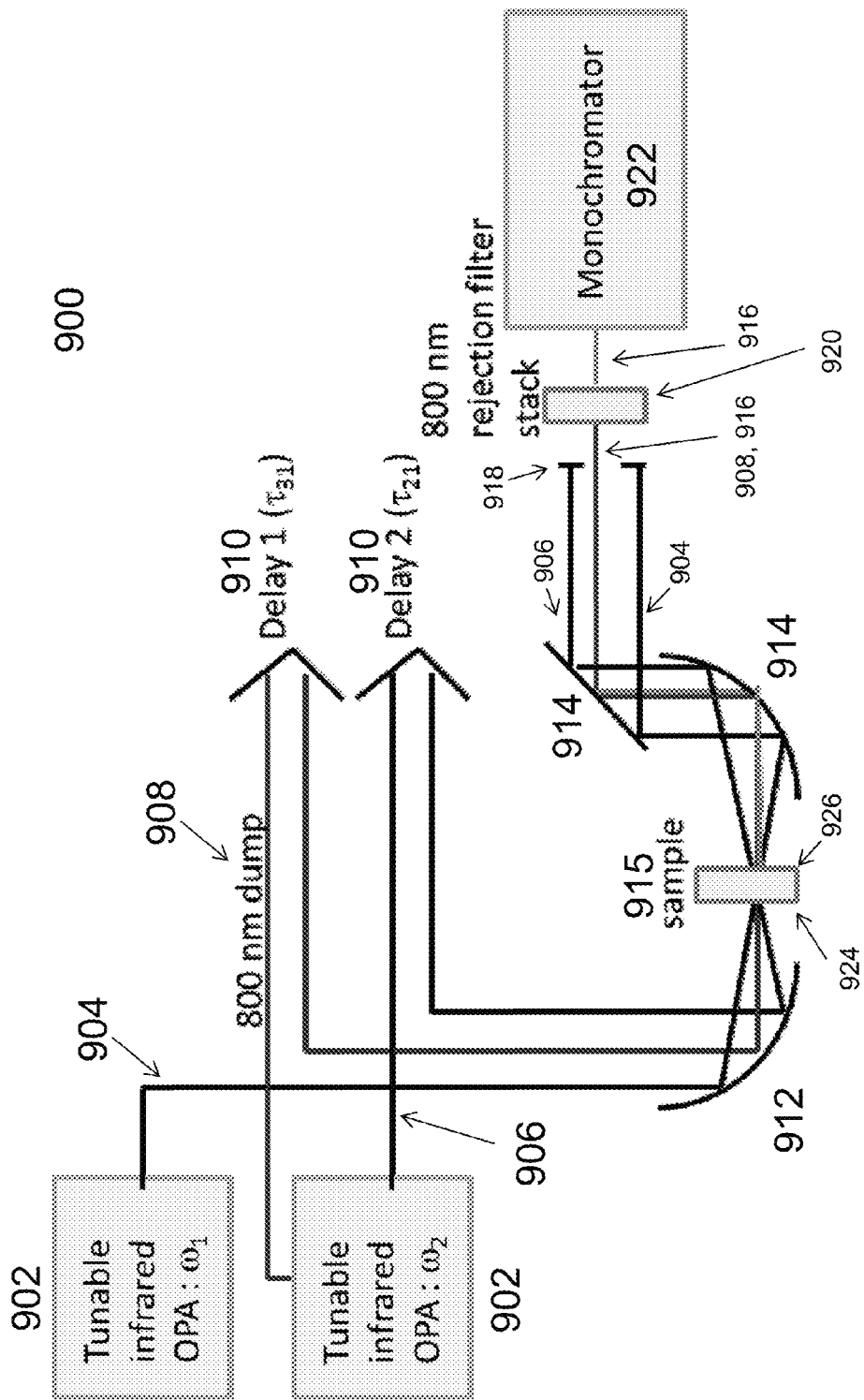
FIG. 9 depicts a schematic of an illustrative system for carrying out triple sum frequency (TSF) or triply resonant sum frequency (TRSF) spectroscopy.
Figure 10:
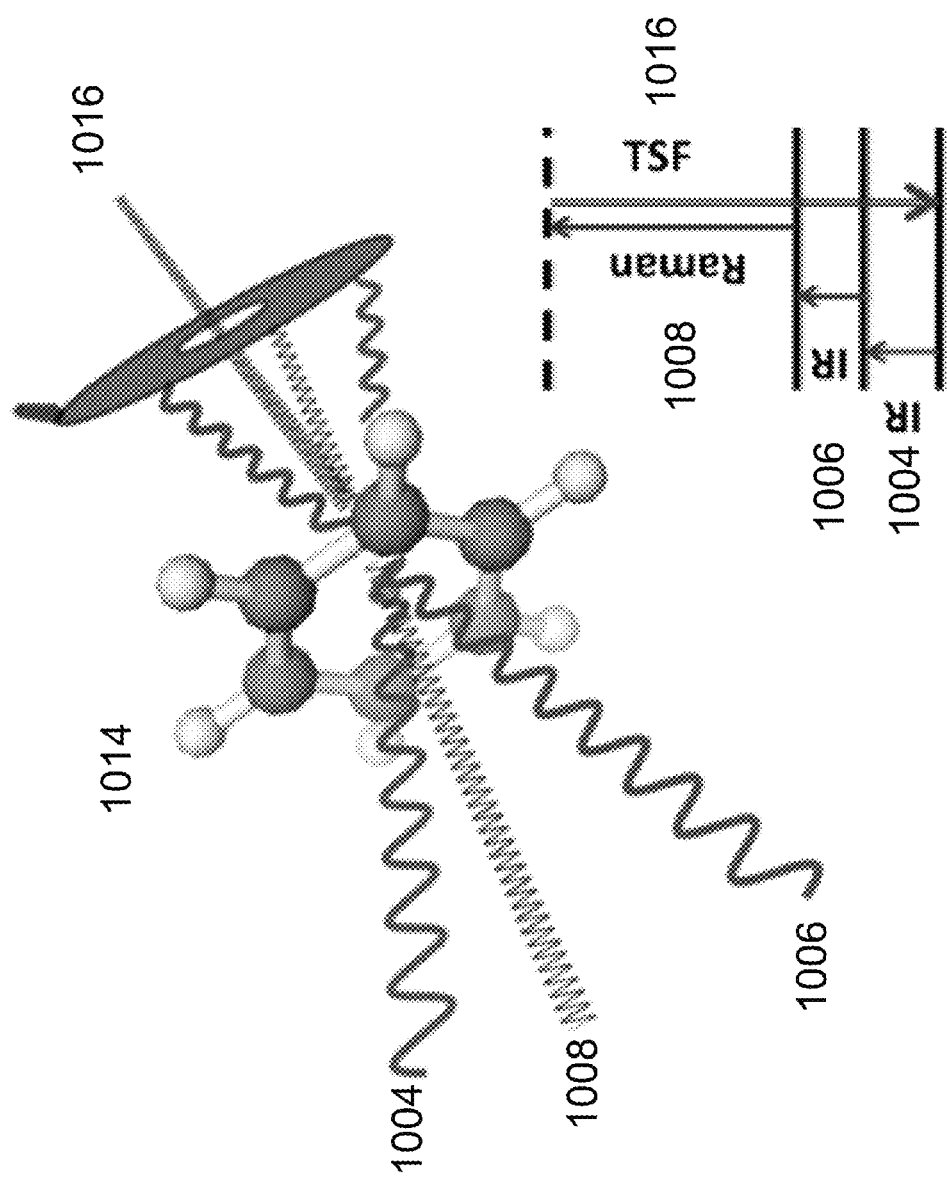
FIG. 10 depicts a schematic of a TSF spectroscopic analysis of benzene according to an illustrative embodiment.

Schematics of the experimental set-up are shown in FIGS. 9 and 10. In FIG. 9, the system 900 includes the light sources 902 which generate a first coherent light pulse 904 having frequency $\omega_1$, a second coherent light pulse 906 having frequency $\omega_2$, and a third coherent light pulse 908 having frequency $\omega_3$. Optics 910 are configured to provide time delays between the coherent light pulses. Optics 912 are configured to focus the coherent light pulses in the sample 915. Optics 914 are configured to direct light generated from the sample (including the coherent output signal 916) or passing through the sample (including the coherent excitation pulses 904, 906 and 908) towards a detector. An aperture 918 blocks the coherent excitation pulses 904 and 906 and a set of optical filters 920 blocks the coherent excitation pulse 908. The coherent output signal 916 is resolved by the monochromator 922. In the system 900, the coherent excitation pulses 904, 906 and 908 enter the sample 915 at the entrance plane 924 and they exit the sample 915 at the oppositely facing exit plane 926, along with the coherent output signal 916 generated in the sample 915.

In FIG. 10, a first coherent light pulse 1004 having frequency $\omega_1$, a second coherent light pulse 1006 having frequency $\omega_2$, and a third coherent light pulse 1008 having frequency $\omega_3$ are focused into a sample 1014 containing benzene. The coherent light pulses excite certain quantum states of benzene to generate a coherent output signal 1016 having frequency $\omega_4$.

Theory

In this section the formalism used to predict spectral intensity and line shape and to simulate multidimensional experiments is presented. Also discussed are the phase-matching restrictions imposed in TSF wave-mixing experiments in condensed media. Finally, comparisons are drawn between pathways in TSF and DOVE or Double Quantum 2D-IR.

FIG. 1A shows the evolution of the states using the wave mixing energy level (WMEL) diagram for TSF CMDS. The time evolution proceeds from left to right. The letters designate the ground, vibrational, and virtual electronic states, the numbers designate the excitation frequency, and the solid and dotted arrows designate transitions that change the ket or bra states, respectively, of the density matrix elements. In the rotating wave approximation where $\rho_{mn} = \tilde{\rho}_{mn} e^{-i\omega_{mn}t}$, the following Liouville equation relates the initial $\rho_{pn}$ and $\rho_{mp}$ density matrix amplitudes to the final $\tilde{\rho}_{mn}$ density matrix amplitude:

$$\dot{\tilde{\rho}}_{mn} = -\Gamma_{mn}\tilde{\rho}_{mn} + \frac{i}{2}\left(\frac{\vec{\mu}_{pm}\cdot\vec{E}}{\hbar}\tilde{\rho}_{pn}e^{i\omega_{mp}t} - \frac{\vec{\mu}_{pn}\cdot\vec{E}}{\hbar}\tilde{\rho}_{mp}e^{i\omega_{pn}t}\right) \quad \text{(Equation 1)}$$

where $\vec{E} = \Sigma_i 1/2 E_i^o(t)(e^{i(\vec{k}_i\cdot\vec{z}_i-\omega_i t)} + e^{-i(\vec{k}_i\cdot\vec{z}_i-\omega_i t)})$; and $E_i^o$, $\vec{k}_i$, are the envelope, wave vector, and frequency of the ith excitation pulse; and $\omega_{mn}$, $\mu_{mn}$, and $\Gamma_{mn}$ are the frequency, transition moment, and dephasing rate of the mn coherence.

The Liouville equations can be simply solved in the steady state to identify the factors controlling the resonance enhancements. The steady state approximates the spectral response for the relatively long 1 ps pulse widths in these experiments. For example, the WMEL pathway shown in FIG. 1A contains the Liouville diagram gg $\xrightarrow{1}$ vg, which describes the evolution of the ground state population to a vg coherence where v is a vibrational state and $\omega_1$ is the excitation frequency. In this case, the resonance enhancement for this transition depends on the minimization of $\Delta_1 \equiv \omega_{vg} - \omega_1 - i\Gamma_{vg}$. The Liouville diagram vg $\xrightarrow{2}$ v'g describes the second interaction in FIG. 1A that creates a v'g coherence using $\omega_2$. The vg coherence frequency at the time of the second interaction will either be the driven frequency, $\omega_1$, if the second pulse temporally overlaps the first, or the free induction decay frequency, $\omega_{vg}$, if it is delayed. If the $\omega_2$ excitation temporally overlaps with the $\omega_1$ excitation pulse, the vg coherence will have a driven component at the $\omega_1$ frequency and the resonance enhancement depends on minimization of $\Delta_2 \equiv \omega_{v'v} - \omega_2 - i\Gamma_{v'g}$. If the $\omega_2$ excitation is delayed from the $\omega_1$ excitation pulse, the vg coherence will have the free induction decay frequency and the resonance enhancement depends on minimization of $\Delta_2 \equiv \omega_{v'v} - \omega_2 - i\Gamma_{v'g}$.

The third interaction is described by the Liouville diagram $v'g \xrightarrow{3} eg$ where the e electronic state represents a virtual sum-over-states in the case of an electronically nonresonant system like benzene, and the eg coherence is responsible for creating the output field. If the $\omega_3$ excitation temporally overlaps with the $\omega_2$ excitation pulse, the v'g coherence will have a driven component at $\omega_2$ (or $\omega_1 + \omega_2$ frequency if the three excitation pulses overlap) and the resonance enhancement depends on minimization of $\Delta_3 \equiv \omega_{ev} - \omega_2 - \omega_3$ $i\Gamma_{eg}$ (or $\Delta_3 \equiv \omega_{eg} - \omega_1 - \omega_2 - \omega_3 - i\Gamma_{eg}$). If the $\omega_3$ excitation does not overlap with the $\omega_2$ excitation pulse, the v'g coherence will have the free induction decay frequency and the resonance enhancement depends on $\Delta_3 \equiv \omega_{ev'} - \omega_3 - i\Gamma_{eg}$. The output coherence frequency will depend upon the relative contributions from the driven and free induction decay components and can range from $\omega_1 + \omega_2 + \omega_3$ if the three excitation pulses overlap in time to $\omega_{v'g} + \omega_3$ if the third pulse is delayed. The third interaction and the output coherence together correspond to a Raman transition involving the gerade v' states.

The transition moments for the infrared absorption transitions are related to the absorption coefficient by the equation $$\alpha = \frac{4\pi \omega N F_1 \mu_{vg}^2 \Gamma_{vg}}{\hbar c |\Delta_{vg}|^2 n^o}(\rho_{gg} - \rho_{vv}) \quad \text{(Equation 2)}$$

where N is the number of oscillators, F is the local field enhancement, $\omega$ is the infrared angular frequency, and $n^o$ is the refractive index. The integrated Raman cross-section is related to the transition moments and the resonance denominator involved in the electronic transitions by the equation $$\sigma = \frac{F_4 n_{ev'} \omega_{ev'}^4 \mu_{ev'}^2 \mu_{eg}^2 \rho_{gg} d\Omega}{2\hbar^2 c^4 n_{eg} |\Delta_{eg}|^2} \quad \text{(Equation 3)}$$

where $\Omega$ is the solid angle of collection. The third order susceptibility for TSF-FWM is related to these same quantities by the equation $$\chi^{(3)} = \frac{NF_4 \mu_{eg} \mu_{gv} \mu_{vv'} \mu_{v'e} \rho_{gg}}{4D\hbar^3 \Delta_1 \Delta_2 \Delta_3} \quad \text{(Equation 4)}$$

where D=6 in the Maker-Terhune convention. The TSF-FWM output intensity in the steady state limit depends on $|\chi^{(3)}|^2$ and is defined by $$I = \frac{256\pi^4 \omega_4^2 D^2 F_4^2 |\chi^{(3)}|^2 l^2}{n^o c^4} M I_1 I_2 I_3 \quad \text{(Equation 5)}$$

where l is the path length, $I_i$ is the intensity of the ith excitation pulse, and M is a factor that corrects for the frequency dependence of the absorption and phase matching effects, $$M = \frac{e^{-\alpha_4 l}[1 - e^{\Delta \alpha l/2}]^2 + 4e^{\Delta \alpha l/2}\sin[\Delta k l/2]^2}{(\Delta \alpha l/2)^2 + (\Delta k l)^2} \quad \text{(Equation 6)}$$

where $\Delta \alpha \equiv \alpha_4 - (\alpha_1 + \alpha_2 + \alpha_3)$ and $\alpha_i$ are the absorption coefficients at the ith excitation or output frequency. In the limit where absorption and refractive index dispersion are negligible, the M factor reduces to the normal sin $c^2$ ($\Delta k l/2$) dependence on the phase mismatch. Substituting Equations 2, 3, 4, and 6 into Equation 5 and fixing $\alpha_3 = \alpha_4 = 0$, as is true in the current experiment, provides an expression that describes both the resonant enhancements of the FWM and the attenuations of the excitation pulse absorption and phase matching effects.

$$I_{TFG} = \frac{2\pi^2 c^2 \omega_4^2}{\hbar^2 \omega_1 \omega_2 \omega_3^4} \frac{n_1 n_2}{n_3} \frac{\alpha_1 \alpha_2 l^2}{\Gamma_{vg} \Gamma_{v'g}} \frac{\sigma}{d\Omega} \quad \text{(Equation 7)}$$

$$(1 - e^{-(\alpha_1 + \alpha_2)l/2})^2 +$$

$$\frac{4e^{-(\alpha_1 + \alpha_2)l/2}\sin|\Delta k l/2|^2}{((\alpha_1 + \alpha_2)l/2)^2 + (\Delta k l)^2} I_1 I_2 I_3$$

The intensity depends strongly on al at the resonances. It is linearly proportional to each al at low absorbance and it saturates at large values. The phase matching dependence is more complex. The refractive index normally decreases from the visible to the mid-IR so the wave vector of the nonlinear polarization $|\vec{k}_p| \equiv (n\omega/c) = |\vec{k}_1 + \vec{k}_2 + \vec{k}_3|$ is smaller than the $\vec{k}_4$ output field so $|\Delta \vec{k} \equiv \vec{k}_4 - \vec{k}_p| > 0$. The anomalous dispersion at the vibrational resonances has additional impact on the phase matching and can improve or degrade the phase matching at different points in the resonance. If $\Delta k l$ is large enough, small asymmetries should appear in the two-dimensional spectral line shape of the transitions. However, since this may occur at longer path lengths than those used in these experiments, and since the TSF CMDS line shapes in the experimental spectra are symmetrical and slices along $\omega_1$ remained relatively consistent for path lengths of 15-150 μm (see FIG. 8A), the effects of the M-factor in frequency and delay scan simulations are neglected.

Spectral and temporal data were modeled by using the approach described by Domcke that numerically integrates Equation 1 under the rotating wave approximation to obtain the evolution of the density matrix elements eventually resulting in the $\rho_{eg}$ output coherence. (See, Gelin, M. F.; Pisliakov, A. V.; Egorova, D.; Domcke, W. A Simple Model for the Calculation of Nonlinear Optical Response Functions and Femtosecond Time-resolved Spectra. *J. Chem. Phys.* 2003, 118, 5287-5301 and Gelin, M. F.; Egorova, D.; Domcke, W. A New Method for the Calculation of Two-pulse Time- and Frequency-resolved Spectra. *Chem. Phys.* 2005, 312, 135-143.) In this method, each pixel of a two-dimensional frequency or delay scan is calculated independently via propagation of the density matrix elements in time. Within the pixel, pulses $E_i(t)$ are introduced with Gaussian envelopes $E_i^o(t)$ centered at their delay time $\tau_i$. They are responsible for transitions between density matrix elements, with m, n, and p subscripts identifying the dephasing rate, transition moment, and frequency of the quantum states defined in FIG. 1A. After integration over the entire excitation period, the $\rho_{eg}$ output signal is Fourier transformed to obtain its frequency distribution. If a monochromator spectrally resolves the output frequencies, the monochromator filter function apodizes the output to give the amplitude of that pixel in the two-dimensional plot.

Parameters of the model include the dephasing times; transition dipoles; pulse frequencies, intensity, and duration; monochromator frequency and resolution; and allowed pathways. This model simulated all of the data presented in order to qualitatively extract lifetimes, transition frequencies, and relative transition dipole moments. Parameters were shared between all plots with the exception of pulse durations (±0.3 ps), which are known to vary across the tuning range, between OPAs, and slightly from day to day.

There are important relationships between TSF-CMDS and DOVE, TRIVE, and 2D-IR CMDS. FIG. 1 compares the Wave Mixing Energy Level (WMEL) diagrams for TSF-CMDS (A), DOVE-CMDS (D-F), and Double Quantum 2D-IR or the TRIVE II/IV $\alpha/\beta$ pathways (B,C). In all cases v is a fundamental vibration, v' is an overtone or combination band, and e is a virtual electronic state denoted by a dashed line. The numbers designate the excitation frequencies (not the time orderings) and the solid and dotted lines designate ket and bra transitions, respectively. The double arrow is the output coherence. The DOVE pathways differ in the time ordering of the interactions and the states involved in the transitions. Typically, the output signal requires that one IR field provides a double quantum excitation of a combination band or overtone and the second IR field provides a single quantum excitation of a fundamental, such that the final output is a single-quantum Raman transition. Pathway 1(D) is a vibrationally enhanced Raman transition and is designated the DOVE-Raman pathway. Pathways 1(E,F) each have two infrared transitions and are designated DOVE-IR pathways. Pathways 1(D) and 1(E) are temporally overlapped and create quantum level interference effects. Pathway 1(F) can provide rephasing or line-narrowing if the inhomogeneous broadening effects of the v and v' states are correlated. This pathway can be temporally isolated from the other pathways. DOVE-CMDS also differed from other FWM pathways in its ability to observe cross-peaks when mechanical anharmonicity is absent and only electrical anharmonicity couples modes. TSF-CMDS also shares this attribute. This attribute can be exploited to provide structural information.

An interesting characteristic of TSF CMDS is its single fully coherent Liouville pathway. In traditional 2D-IR, the $\vec{k}_1 - \vec{k}_2 + \vec{k}_3$ or $-\vec{k}_1 + \vec{k}_2 + \vec{k}_3$ pathways contain parametric and nonparametric processes that destructively interfere. If mechanical anharmonicity is absent, these processes exactly cancel. Similarly, DOVE pathways (D) and (E) in FIG. 1 have the same time ordering but opposite signs and can cancel if mechanical anharmonicity is absent. The pathway in FIG. 1F has a different time ordering that is unique and is not canceled if mechanical anharmonicity is absent. Its intensity would then depend on the electrical anharmonicity. Similarly, the TSFCMDS pathway is unique and is not canceled if the vibrational modes are mechanically harmonic. The intensity would also then depend on the electrical anharmonicity and can be large if $|(\partial^{(n)}\mu)/(\partial Q^{(n)})>>0|$, as can be true for vibronic transitions. Additionally, TSF-CMDS does not involve populations so population relaxation will not create new peaks. The pathway is fully coherent and should be capable of isolating the coherent dynamics of coherence transfer processes.

The symmetry of the states appearing in the TSF spectrum is constrained by benzene's inversion symmetry. The modes excited by the first interaction have ungerade symmetry and are the same as those in the infrared absorption spectrum. The symmetry of the overtone or combination band states excited by the second interaction is defined by the direct product of the overtone or combination band and must have gerade symmetry for a centrosymmetric molecule. The third interaction excites a double quantum Raman transition where the initial and final states have the gerade symmetry required by the gerade symmetry of the polarizability. Therefore the cross-peak $\omega_1$ frequencies correspond to the states observed in the infrared spectrum while the $\omega_2$ frequencies correspond to the Raman spectra of overtones, combination bands, and states coupled to them.

By comparison, DOVE-CMDS has two possible symmetry pathways. DOVE-IR demands both fundamental and overtone/combination band transitions excite modes with ungerade symmetry since each transition involves absorption from the ground state. The Raman transition is then an allowed transition between two ungerade states. DOVE-Raman, however, accesses double quantum ungerade states in the first transition but single quantum gerade states in the second. The third interaction excites an allowed transition between two gerade states. The result is that the combination band and overtone states in TSF-CMDS have exactly the opposite parity from those in DOVE-CMDS. Additionally, the output Raman transition occurs as an overtone or combination band transition in TSF-CMDS and a fundamental transition in DOVE-CMDS. Note that the overtone and combination band states in TRIVECMDS and 2D-IR double quantum pathways involve states of the same parity as TSF-CMDS. Note also that the electronic states involved in the DOVE-CMDS output transition have gerade symmetries while those in the TSF-CMDS output transition have ungerade symmetries.

Results

Figure 2B:
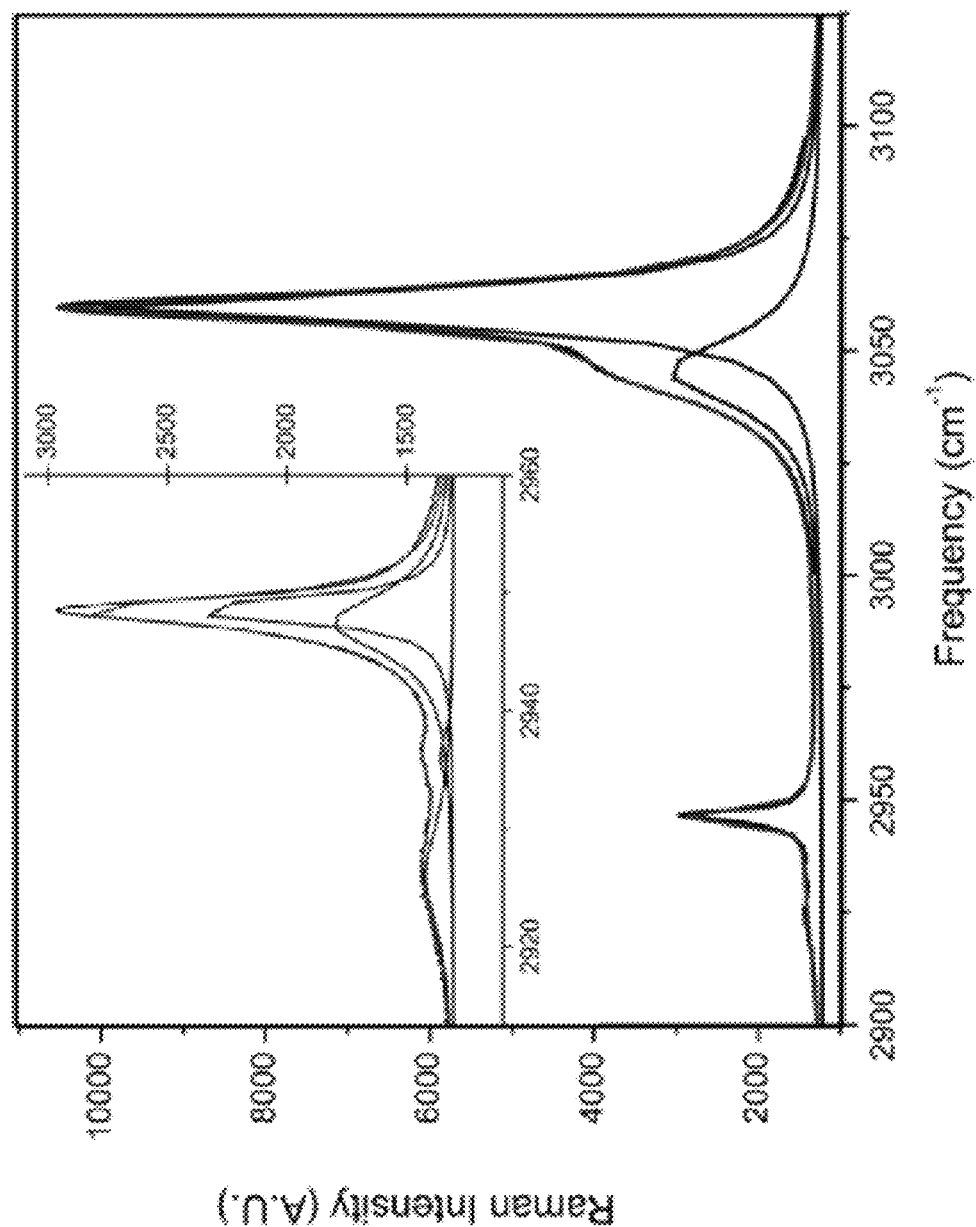
FIG. 2B shows benzene's Raman spectrum, with the inset expanded around the $2v_{13}$ overtone region (all assignments follow Herzberg notation). (See, Bertie, J. E. John Bertie's Download Site. 2011; http://www.ualberta.ca/jbertie/JBDownload.HTM.) Data are in black, individual Lorentzian states are in blue, and fitted sums are in red.

FIG. 2 shows the 1D infrared and Raman vibrational spectra of benzene. These spectra have been fit to a sum of Lorentzian line shapes and the parameters for those fits are given in Table 1, with the $\tau$ value calculated from $\Gamma$ using Lorentzian broadening. Fitting the feature at 2948 cm$^{-1}$ required two Lorentzians and attempts to fit this region to just the two most prominent peaks resulted in migration of the weaker Lorentzian to the 2947 cm$^{-1}$ location. Therefore there truly are two transitions here, one of which is quite narrow. (Frequencies of Raman active C—H modes are inconsistent in the literature, with many sources agreeing with the 3047/3061 cm$^{-1}$ pair that have been measured here, and many finding 3057/3074 cm$^{-1}$ instead.

TABLE 1

Lorentzian Properties of Benzene Transitions

| type | Herzberg designation | freq (cm$^{-1}$) | $\Gamma$ (HWHM) (cm$^{-1}$) | $\tau$ (ps) | intensity (arb) |
|---|---|---|---|---|---|
| IR | $v_{13}$ | 1478.3 | 3.0 | 1.8 | 1 |
|  | $v_4 + v_{11}$ | 1527.9 | 10 | 0.53 | 0.14 |
|  | $v_{12}$ | 3048 |  |  |  |
| Raman | $v_9 + v_{14}$ | 2926.0 | 5.6 | 0.94 | 0.017 |
|  |  | 2936.0 | 2.5 | 2.1 | 0.0037 |
|  |  | 2947.4 | 3.1 | 1.7 | 0.040 |
|  | $2v_{13}$ | 2948.5 | 1.1 | 4.8 | 0.035 |
|  | $v_{15}$ | 3047.2 | 9 | 0.59 | 0.42 |
|  | $v_1$ | 3061.4 | 4.5 | 1.2 | 1 |

Figure 3:
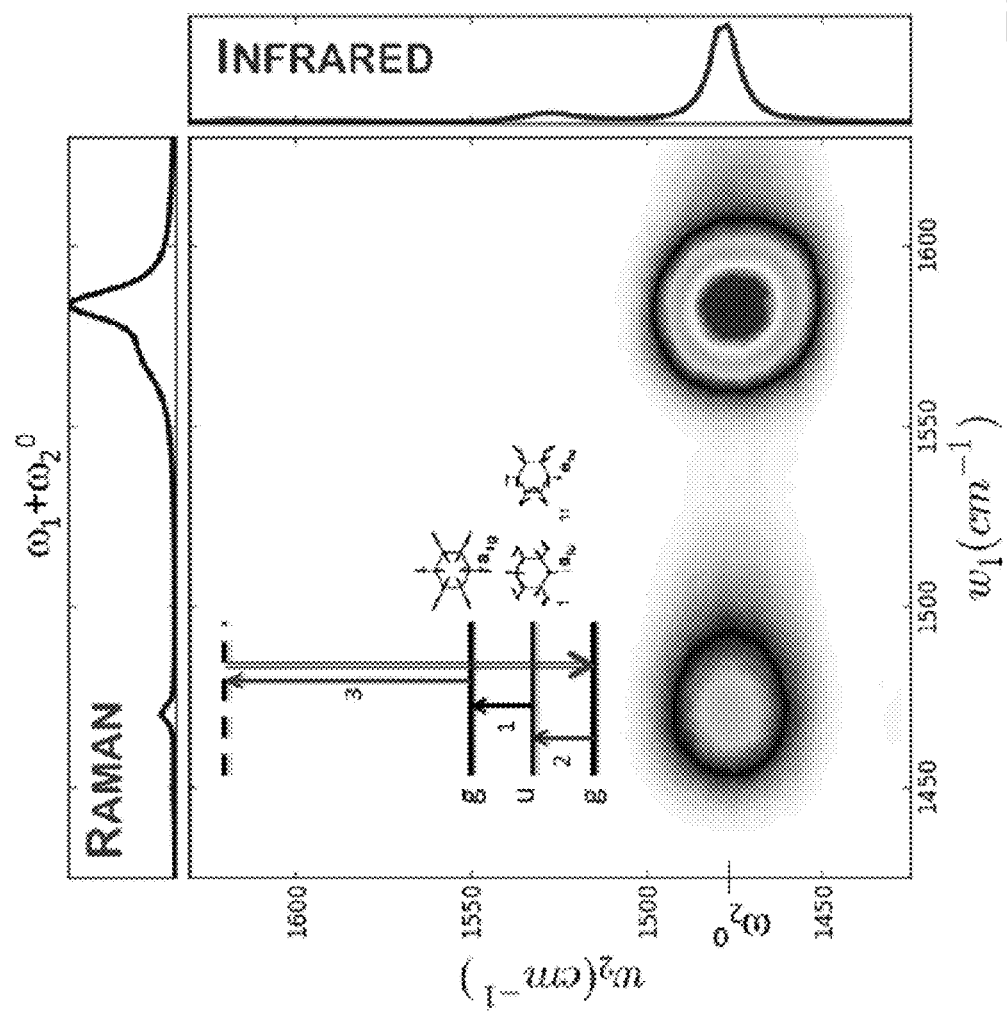
FIG. 3 shows a 2D TSF scan of benzene (intensity level) at $\tau_{21}$=1.2 ps, $\tau 31$=1 ps. The WMEL diagram shows the time ordering of the three excitation pulse resonances from left to right. The numbers identify the excitation frequency of each pulse and the pairs of numbers identify the time delay between the pulses. Raman and IR spectra of FIG. 2 are aligned with the $\omega_1$ and $\omega_2$ axes, with the Raman spectrum shifted downward by the $v_{13}$ fundamental frequency, 1478 cm$^{-1}$ ($\omega_2^0$). Benzene normal mode images are taken from Page et al., and illustrate the ungerade nature of the benzene modes along $\omega_2$ and the gerade nature of the modes accessed by $\omega_1+\omega_2$. (See, Page, R. H.; Shen, Y. R.; Lee, Y. T. Infrared-Ultraviolet Double-Resonance Studies of Benzene Molecules in a Supersonic Beam. *J. Chem. Phys.* 1988, 88, 5362-5376.)

FIG. 3 shows a 2D TSF frequency spectrum of the intensity dependence on $\omega_1$ and $\omega_2$ with time delays $\tau_{21}$=1.2 ps=$\tau_{31}$=1 ps and broad-band filters to isolate the output frequency. With this set of time delays, $\omega_2$ interacts first and excites the C═C ring-breathing mode at 1478 cm$^{-1}$, called $v_{13}$ in the Herzberg notation, that will be used throughout this paper. $\omega_1$ comes 1.2 ps later and excites an overtone or coupled state at ~1478 and 1584 cm$^{-1}$. The visible beam interacts 1 ps later and induces the Raman transition that creates the output beam and returns the system to the ground state. As discussed earlier, the output signal contains contributions from both the driven coherence created during the interactions with the excitation pulses and the free induction decay of the coherence resulting after the excitation pulses. The time delays are long enough that the free induction decay components will dominate.

The main fundamental transition of FIG. 3 is clearly the bright $v_{13}$ mode. As expected, its overtone state is observed where $\omega_2$ is also ~1478 cm$^{-1}$. However, the requirement of the second transition having fundamental ungerade character offers no fundamental vibrational state for assignment of the cross-peak at ~1584 cm$^{-1}$, i.e. this is not a combination band. In DOVE-CMDS, the $v_{16}$=1600 cm$^{-1}$ $E_{2g}$ state is observed due to its different selection rules, but TSF-CMDS is insensitive to this symmetry. (See, Donaldson, P. M.; Guo, R.; Fournier, F.; Gardner, E. M.; Barter, L. M. C.; Barnett, C. J.; Gould, I. R.; Klug, D. R.; Palmer, D. J.; Willison, K. R. Direct Identification and Decongestion of Fermi Resonances by Control of Pulse Time Ordering in Two-dimensional IR Spectroscopy. *J. Chem. Phys.* 2007, 127, 114513.) Therefore the state observed must be that at the sum frequency 3061 cm$^{-1}$ itself, the $v_1$ $A_{1g}$ C—H stretch, and access to this state arises from the Fermi resonance between the $v_{13}$ mode and the C—H modes.

Figure 4A:
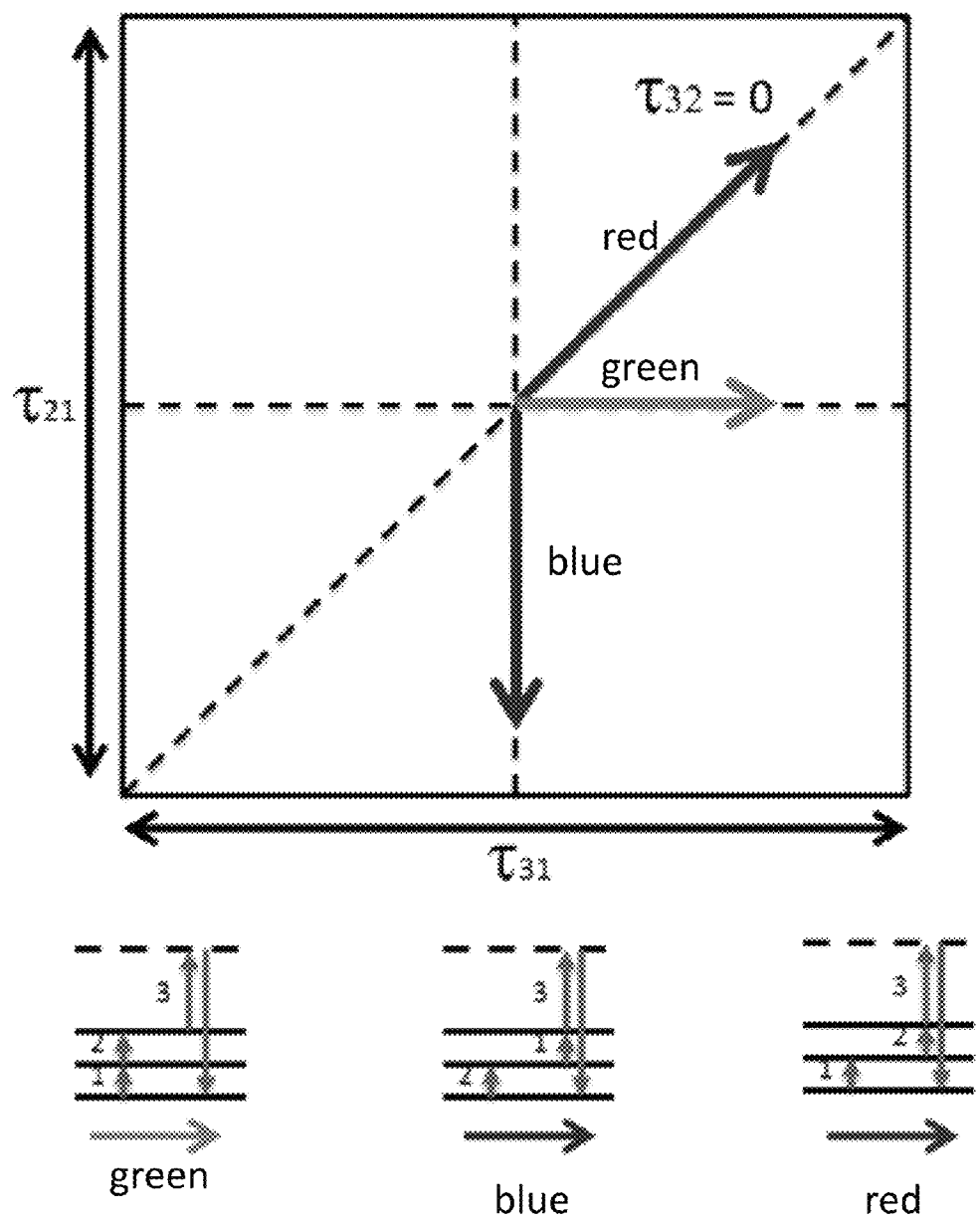
FIG. 4A is a schematic that describes pathways observed along each axis in a 2D delay scan. In observation of only $\vec{k}_1 + \vec{k}_2 + \vec{k}_3$ phase-matching output, the red and/or blue arrows trace out the fundamental vibrational dephasing rate depending on whether the first interaction involves $\omega_2$ or $\omega_1$, respectively, and the green arrow traces out the overtone or coupled state dephasing rate.

It is also important to understand how the spectral features depend on the time delays between the excitation pulses and on contributions from different phase matching conditions. Since the $\omega_1$ and $\omega_2$ frequencies are close to each other, the $2\vec{k}_1+\vec{k}_3$ and $2\vec{k}_2+\vec{k}_3$ phase matching conditions can also contribute to the spectrum if spatial discrimination from the $\vec{k}_1+\vec{k}_2+\vec{k}_3$ diagonal peak is not adequate. FIG. 4A is a schematic of how the different coherence pathways change for different excitation pulse delay times and time orderings. The abscissa is the time delay between the beams with frequencies $\omega_3$ and $\omega_1$, $\tau_{31} \equiv \tau_3 - \tau_1$, and the ordinate is the time delay between the beams with frequencies $\omega_2$ and $\omega_1$, $\tau_{21} \equiv \tau_2 - \tau_1$. The dotted lines define the regions for each of the six possible time orderings of the three excitation pulses. The bottom three WMEL diagrams show the time orderings and resonances when the time delays are scanned along the directions of the corresponding green, blue, and red arrows in the schematic.

Figure 4B:
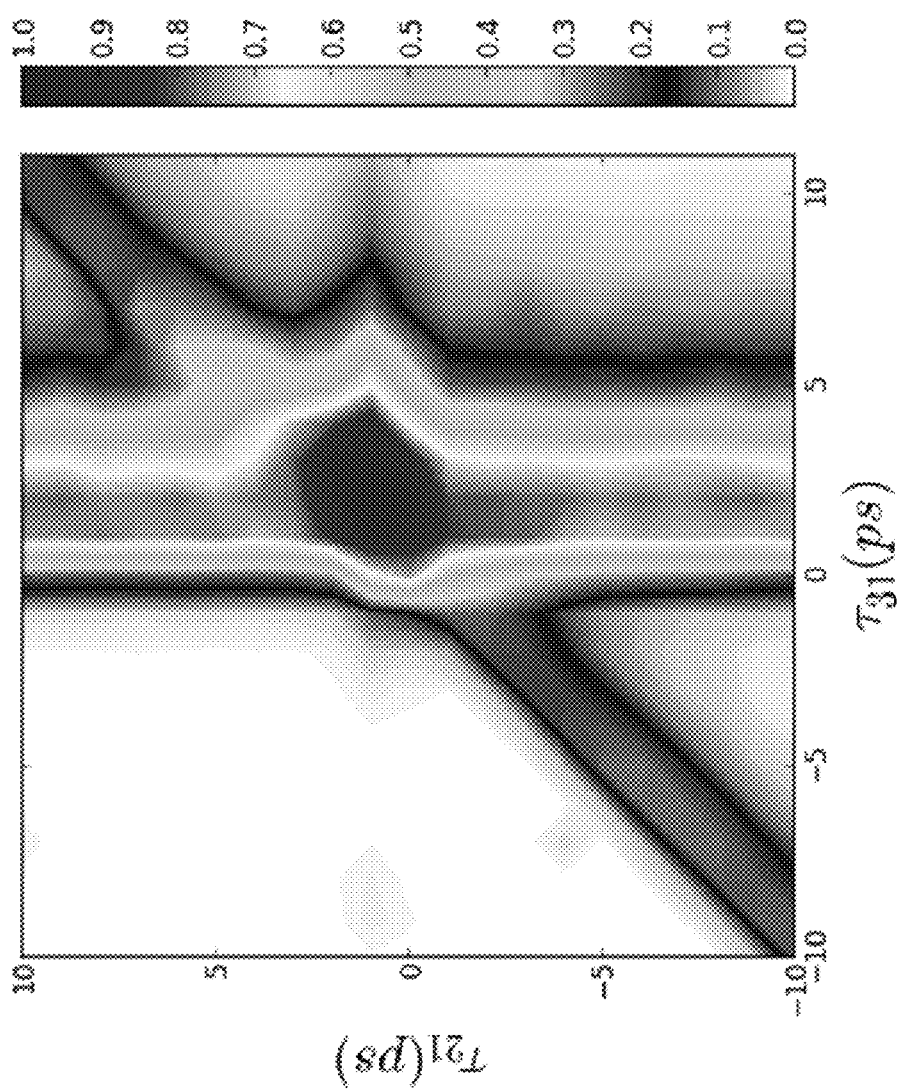
FIG. 4B shows a delay scan of a 15 nm benzene sample with $\omega_1 = \omega_2 = 1475$ cm$^{-1}$ where $2\vec{k}_1 + \vec{k}_3$, $2\vec{k}_2 + \vec{k}_3$, and $\vec{k}_1 + \vec{k}_2 + \vec{k}_3$ TSF signals are all collected. The vertical stripe represents $2\vec{k}_1 + \vec{k}_3$ as it occurs at $\tau_{31} = 0$ and the diagonal stripe represents $2\vec{k}_2 + \vec{k}_3$ as it traces out $\tau_{21} = \tau_{31}$.

FIG. 4B shows an example of a 2D scan of the $\tau_{21}$ and $\tau_{31}$ time delays at the diagonal peak where $(\omega_1, \omega_2)$=(1475, 1475) cm$^{-1}$ when there is no spatial discrimination between the three phase matching contributions. As depicted in FIG. 4A, the vertical feature results from the $2\vec{k}_1+\vec{k}_3$ phase matching. It has no dependence on the $\omega_2$ pulse time delay. The long diagonal feature results from the $2\vec{k}_2+\vec{k}_3$ phase matching and it has no dependence on the $\omega_1$ time delay. The peak at the intersection between these phase matching features arises from the $\vec{k}_1+\vec{k}_2+\vec{k}_3$ phase matching and it depends on the presence of all three pulses. The peak decays away quickly along the upper left diagonal (see the red arrow in FIG. 4A) because the vg coherence dephases as the $\omega_2$ and $\omega_3$ beams are delayed from the $\omega_1$ excitation (see right-most WMEL diagram). It also decays away quickly along the positive horizontal axis (see the green arrow in FIG. 4A) because the vg coherence dephases as the $\omega_3$ beam is delayed from the $\omega_1$ and $\omega_2$ excitations (see leftmost WMEL diagram).

To determine an accurate value for the $v_{13}$ mode anharmonicity, a 2D frequency scan was collected with the aperture adjusted to pass the $\vec{k}_1+\vec{k}_2+\vec{k}_3$ beam and a small amount of the $2\vec{k}_2+\vec{k}_3$ beam. This change makes it possible to determine the small overtone anharmonicity by directly comparing the difference in peak position on the same axis with the same calibration.

Figure 5:
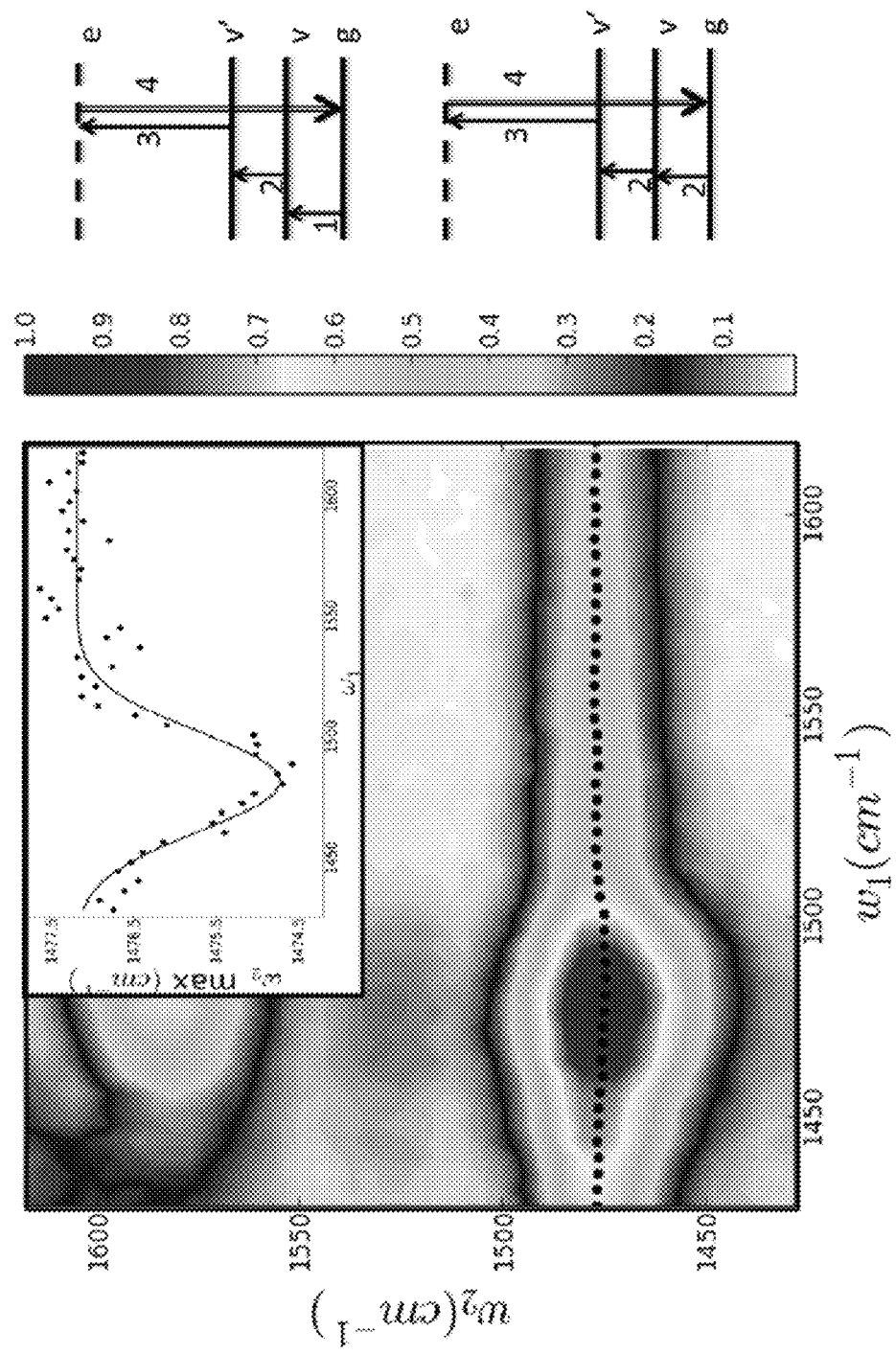
FIG. 5 shows a 2D TSF scan collected at $\tau_{21} = 1.5$ ps, $\tau_{31} = 3$ ps, presented as $(\text{Int})^{1/2}$ for clarity. Both $\vec{k}_1 + \vec{k}_2 + \vec{k}_3$ and $2\vec{k}_2 + \vec{k}_3$ TSF signal has been admitted to the detector (WMEL diagrams to right). Black dots indicate Gaussian peak maxima of each $\omega_1$ slice; these are expanded in the inset and fit to another Gaussian. The cross-peak maximum is corrected further by subtraction of the $2\omega_2 + \omega_3$ line.

FIG. 5 shows the result of this experiment. The time delays are similar to those in FIG. 3 but with $\omega_1$ and $\omega_2$ permuted such that $\omega_2$ comes second to excite the Fermi overtone states. The color bar denotes the signal amplitude, i.e., the square root of the output intensity. The spectrum shows the same two peaks as FIG. 3 and a horizontal feature from the signal that does not depend on $\omega_1$ and corresponds to the output coherence wave vector $\vec{k}_{4'}=2\vec{k}_2+\vec{k}_3$. The $\vec{k}_{4'}$ signal reaches a maximum along $\omega_2$ at $(2\omega_{vg}-\delta)/2$, where $\delta$ is the overtone anharmonicity since the $\vec{k}_2$ beam provides both the fundamental and overtone transitions. The $\vec{k}_4$ signal reaches a maximum at $\omega_{vg}-\delta$, the frequency of the overtone transition. There should therefore be a shift of $\delta/2$ between the $\vec{k}_4$ and $\vec{k}_{4'}$ central frequencies. The FIG. 5 inset shows the expected decrease in the $\omega_2$ peak frequency at the diagonal peak due to its shift toward the anharmonic overtone frequency.

However, this diagonal region still contains contribution from the $2\vec{k}_2+\vec{k}_3$ pathway, so it was necessary to isolate the $\vec{k}_4$ contribution from $\vec{k}_{4'}$ to accurately determine its peak value. This separation was achieved by finding the average profile of the horizontal feature at frequencies removed from the diagonal peak and subtracting that from the diagonal peak region in order to fit the remaining $\vec{k}_4$ feature. Diagonal peak $\omega_2$ slices were then fit to accurately define the peak $\omega_2$ frequency as a function of $\omega_1$. These central values varied smoothly and showed that the peak center occurs at 1473.7 cm$^{-1}$. The difference between the $\vec{k}_4$ and $\vec{k}_{4'}$ peak positions ($\delta/2$) is 3.5 cm$^{-1}$ so $\delta$=7 cm$^{-1}$. This anharmonicity agrees well with the data in Table 1, since the difference between the $2*v_{13}$ frequency (2956.6 cm$^{-1}$) and the Raman overtone (2948.5 cm$^{-1}$) is an 8 cm$^{-1}$ anharmonicity. These data provide further confirmation of the contested assignment of this band.

Figure 6A:
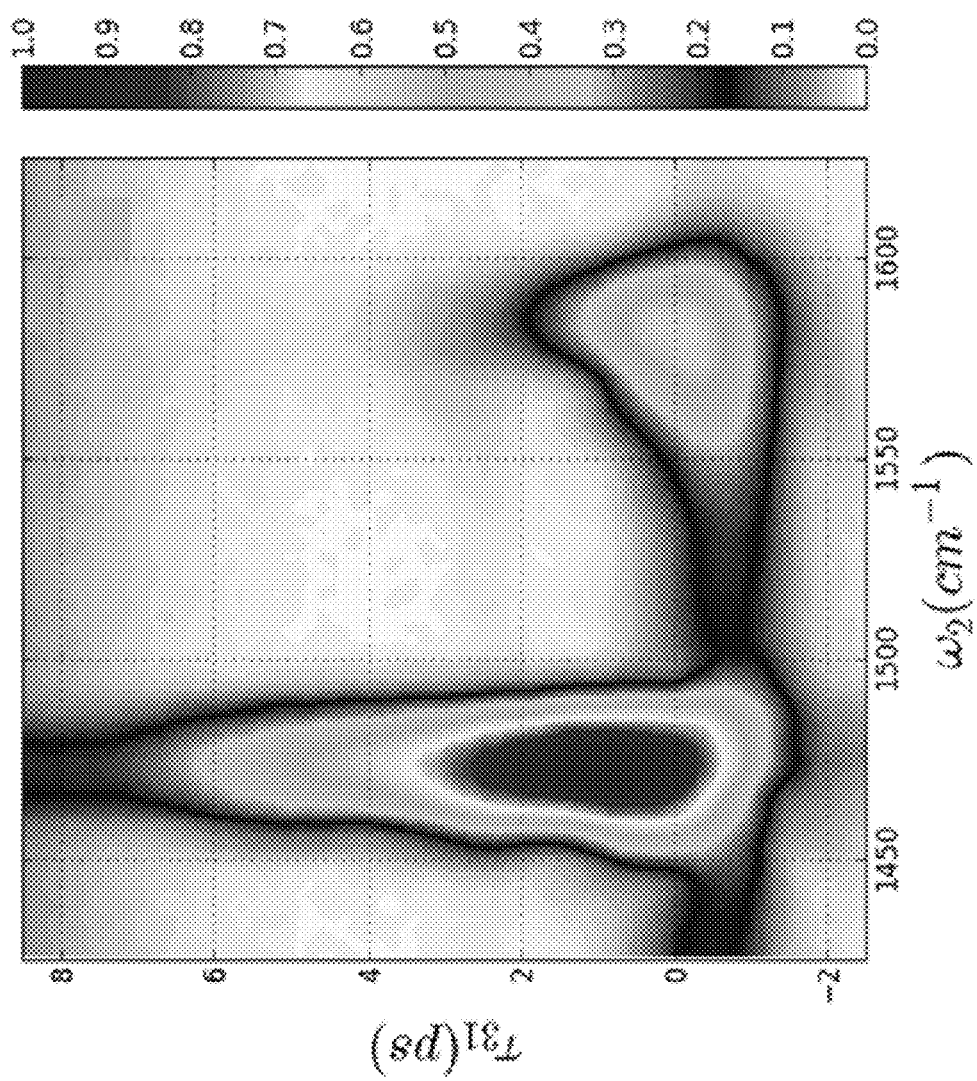
FIG. 6A shows a Wigner plot collected with $\tau_{21} = 1$ ps, $\omega_1 = 1480$ cm$^{-1}$, and $\omega_m = \omega_1 + \omega_2 + \omega_3$.
Figure 6B:
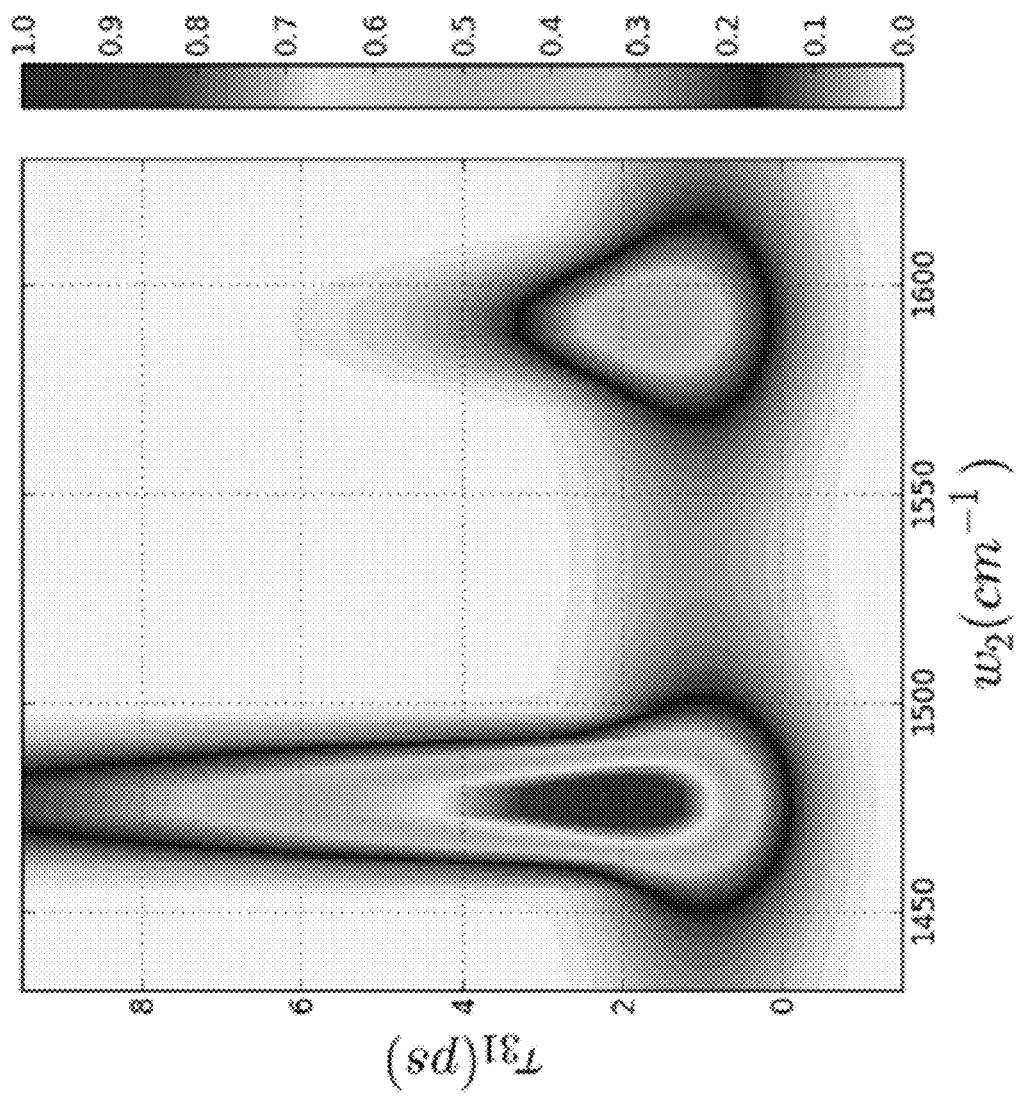
FIG. 6B shows a model of the same, using dephasing rates predicted in Table 1.

The Wigner plot in FIG. 6 traces out the overtone and cross-peak lifetimes of the TSF states. The beating on the left side of the $2v_{13}$ peak is attributed to an unresolved, lower energy mode that is too weak to observe directly but becomes observable as beating when the monochromator eliminates most of the contribution of the prominent 2948 cm$^{-1}$ transition.

Discussion

The two peaks observed in the TSF-CMDS spectra are attributed to a Fermi resonance of the $E_{1u}$ overtone ($2v_{13}$) with the benzene $A_{1g}$ C—H stretch mode ($v_1$). The Fermi resonances of benzene's ungerade C—H stretch modes are well-studied and play an important role in DOVE-CMDS 2D spectra. (See, Donaldson, P. M.; Guo, R.; Fournier, F.; Gardner, E. M.; Barter, L. M. C.; Barnett, C. J.; Gould, I. R.; Klug, D. R.; Palmer, D. J.; Willison, K. R. Direct Identification and Decongestion of Fermi Resonances by Control of Pulse Time Ordering in Two-dimensional IR Spectroscopy. *J. Chem. Phys.* 2007, 127, 114513.) Calculations show that Fermi resonances create a tetrad of states where the $E_{1u}v_{12}$ mode mixes with the $v_{13}+v_{16}$, $v_2+v_{13}+v_{18}$, and $v_3+v_{10}+v_{18}$ combination bands that appear in infrared spectra. Three of these states are allowed in DOVEFWM spectra of the CH mode region and two are observed. (See, Donaldson, P. M.; Guo, R.; Fournier, F.; Gardner, E. M.; Barter, L. M. C.; Barnett, C. J.; Gould, I. R.; Klug, D. R.; Palmer, D. J.; Willison, K. R. Direct Identification and Decongestion of Fermi Resonances by Control of Pulse Time Ordering in Two-dimensional IR Spectroscopy. *J. Chem. Phys.* 2007, 127, 114513.) The absence of other peaks indicates their minimal $v_{13}$ and $v_{16}$ character, as coupling to these fundamental modes would be required for significant DOVE signal. Consideration of this transition strength along with DFT studies therefore led to assignment of Fermi mixing coefficients to members of the ungerade C—H tetrad.

The states appearing in the TSF-CMDS spectra of the current study are attributed to a similar Fermi resonance between the gerade $v_1$ $A_{1g}$ C—H stretch mode and the $2v_{13}$ overtone. The $E_{1u}$ symmetry of the $v_{13}$ mode results in a symmetric direct product for its overtone of $A_{1g}+E_{2g}$, so the first of these allows Fermi mixing with the C—H stretch at 3061 cm$^{-1}$. It is interesting to note that the C—H stretch at 3047 cm$^{-1}$ ($v_{12}$) is $E_{2g}$ and therefore could undergo mixing with the other portion of the $v_{13}$ overtone, and yet this cross-peak does not appear in our spectra. Assuming $v_1$ and $2v_{13}$ are the only two states involved in the $A_{1g}$ mixing, the Fermi resonance is described by $$\Psi_+ = \cos\left(\frac{\theta}{2}\right)|v_1\rangle + \sin\left(\frac{\theta}{2}\right)|2v_{13}\rangle \quad \text{(Equation 8)}$$

$$\Psi_- = \cos\left(\frac{\theta}{2}\right)|2v_{13}\rangle + \sin\left(\frac{\theta}{2}\right)|v_1\rangle \quad \text{(Equation 9)}$$

where $\Psi_\pm$ are the eigenstates resulting from Fermi mixing between states $v_1$ and $2v_{13}$ and $\theta$ is the mixing angle resulting from the coupling, $V_F$, by $$\theta = \mathrm{atan}\left(\frac{2V_F}{\hbar(\omega_{v_1} - \omega_{2v_{13}})}\right) \quad \text{(Equation 10)}$$

The transition dipoles for the eigenstates are given by $$\vec{\mu}_+ = c_1 \vec{\mu}_{v_1} + c_2 \vec{\mu}_{2v_{13}} \quad \text{(Equation 11)}$$

$$\vec{\mu}_- = c_1 \vec{\mu}_{2v_{13}} + c_2 \vec{\mu}_{v_1} \quad \text{(Equation 12)}$$

where $c_1 = \cos(\theta/2)$ and $c_2 = \sin(\theta/2)$.

The TSF enhancement in the $\rho_{vg} \rightarrow \rho_{v'g}$ transition relies dominantly on the overtone $2v_{13}$ absorption strength, while the $\rho_{v'g} \rightarrow \rho_{eg}$ transition relies dominantly on the $v_1$ Raman transition strength. Therefore, since the 2948 cm$^{-1}$ peak has the lower energy and corresponds to $\Psi_-$, the peak intensity scales as $|c_1|^2$ in the second resonance enhancement and $|c_2|^2$ in the third resonance enhancement. Similarly the 3061 cm$^{-1}$ peak corresponds to $\Psi_+$ and scales as $|c_2|^2$ in the second resonance enhancement and $|c_1|^2$ in the third resonance enhancement. These relationships between the transition moments are part of the simulation and the resulting intensities agree well with experiment.

There are two peaks in the Raman spectrum that have the same frequencies observed in this example. As described above, their difference in intensity and splitting depend on the $V_F$ and $\Delta\hbar\omega$. Both quantities are unknown as the overtone frequency prior to Fermi mixing is likely not exactly twice the fundamental frequency. If one assumes the relative Raman intensities of $\Psi_\pm$ depend entirely upon their $\vec{\mu}_{v_1}$ character, then one relationship between $V_F$ and $\Delta\hbar\omega$ can be defined via the mixing angle $\theta$. A second relationship can be defined by using the frequencies of $\Psi_\pm$. Solving this system of equations leads to a coupling energy of 19 cm$^{-1}$. This results in only a ~3 cm$^{-1}$ shift on each local mode and therefore the other 4-5 cm$^{-1}$ of shift on the 2948 cm$^{-1}$ mode is a result of mechanical anharmonicity.

Theoretical calculations of cubic anharmonicity in benzene have been done in the past by finite difference method by using DFT with a B3LYP functional and TZ2P basis set, as well as by analytic derivatives with a HartreeFock DZP potential using Moller-Plesset perturbation theory. Anharmonic force constants between these methods agreed within 5% for the Fermi couplings of the $v_{13}$ overtone with both the $v_1$ and $v_{12}$ C—H stretches, and resulted in coupling energies of 25 cm$^{-1}$ for the former and 12 cm$^{-1}$ for the latter. This general trend is in agreement with the observation here of only a $v_1$ cross-peak. The fact that the $v_{12}$ state is not detected at all, may be due to a combination of the weak coupling from the $v_{13}$ fundamental, the possibility of error in that predicted coupling, the weaker Raman transition strength of $v_{12}$, and the relatively broad spectral bandwidth of the pulses used.

The Wigner plot and simulation in FIG. 6 trace out the overtone and cross-peak lifetimes of the TSF states. Experimental error in setting the time delay zero point led to an offset between the experimental and simulated data. To match the data, the $\tau_{21}$ and $\tau_{31}$ time delays in the simulated data were translated by 1 ps relative to experimental data. Similar errors are also responsible for changes in relative intensity observed between the two peaks in FIGS. 6 and 3. This difference arises because the 1584 cm$^{-1}$ peak intensity relies on the $\omega_2$ interaction occurring after the $\omega_1$ interaction while the 1478 cm$^{-1}$ peak has contributions from both time orderings. The relative intensities therefore depend on $\tau_{21}$. In addition, the differences in the dephasing times of the states created by the second resonance make the relative intensities dependent on $\tau_{31}$ so the relative intensities are sensitive to errors in both delay times. In the Wigner plot, lifetimes predicted by the Raman linewidths reported in Table 1 are in good agreement with experimental data. The beating observed on the red side of the overtone-dominated Fermi resonance state is attributed to the presence of a secondary state. It is notable that the $2v_{13}$ overtone has a surprisingly long dephasing time of 4.5 ps, as compared to the $v_{13}$ fundamental lifetime of 1.8 ps. It should be noted that assignment of this Raman peak was debated in the literature and thought to be a combination band unrelated to the $v_{13}$ state: $v_2 + v_3 + v_8$. (See, Gee, A. R.; Robinson, G. W. Raman Spectrum of Crystalline Benzene. *J. Chem. Phys.* 1967, 46, 4847-4853.) However, the strong coupling between this mode and the fundamental, as well as the match of unusual lifetime between the Raman and TSF spectra, makes the assignment definitive.

It was surprising that the TSF-CMDS intensity is larger than the comparable DOVE-CMDS signal, especially since the $\vec{K}_4 = \vec{K}_1 + \vec{K}_2 + \vec{K}_3$ phase matching condition cannot be phase matched for normal dispersion. To understand this result, simple models incorporating the M-factor using known values for frequency-dependent indices of refraction and absorption coefficients were undertaken. The results demonstrate that the benzene peak is not affected by phase mismatch in a way that significantly distorts the line shape (FIG. 7) or attenuates the signal at long path lengths (FIG. 8).

FIG. 7 shows a set of simulations that model the effects of absorption and anomalous dispersion on the CMDS efficiency and spectral line-shapes using Equation 7 and the benzene refractive indices and absorption coefficients measured by Bertie. (See, Bertie, J. E.; Jones, R. N.; Keefe, C. D. Infrared Intensities of Liquids 0.12. Accurate Optical Constants and Molar Absorption Coefficients Between 6225 and 500 cm$^{-1}$ of Benzene at 25° C., from Spectra Recorded in Several Laboratories. *Appl. Spectrosc.* 1993, 47, 891-911 and Bertie, J. E.; Lan, Z. The Refractive Index of Colorless Liquids in the Visible and Infrared—Contributions from the Absorption of Infrared and Ultraviolet Radiation and the Electronic Molar Polarizability Below 20500 cm$^{-1}$. *J. Chem. Phys.* 1995, 103, 10152-10161.) It assumes fixed field strengths and that $\omega_1$ provides the fundamental transition and $\omega_2$ the overtone. It is not a numerical integration of the Schrodinger equation and does not take into account spectral width of the exciting fields, causing its narrowness relative to FIG. 3. The absorption coefficients in the numerator of Equation 7 create a resonant enhancement that offsets the attenuation described by the M-factor. The importance of the M-factor depends on the sample path length, the absorption coefficients, and the phase mismatch. The model assumes that insignificant population is removed from the ground state, such that excited state absorption provides the multiplicative enhancement effects as $\alpha_2'$, but that the field-depleting absorption effects follow the ground state absorption profile even on the $\omega_2$ axis ($\alpha_2$ in $e^{-\alpha_2}$). The absorption from the exponential term, $e^{-\alpha_1}$, in Equation 7 causes attenuation of the peak intensity while the anomalous dispersion from the $v_{13}$ mode causes attenuation in the $\omega_1 > 1478$ cm$^{-1}$ region because of the larger phase-mismatch. The depletion on $\omega_2$ occurs at a displaced value from the TSF peak due to anharmonicity, and therefore does not affect line shape in this instance.

Figure 7A:
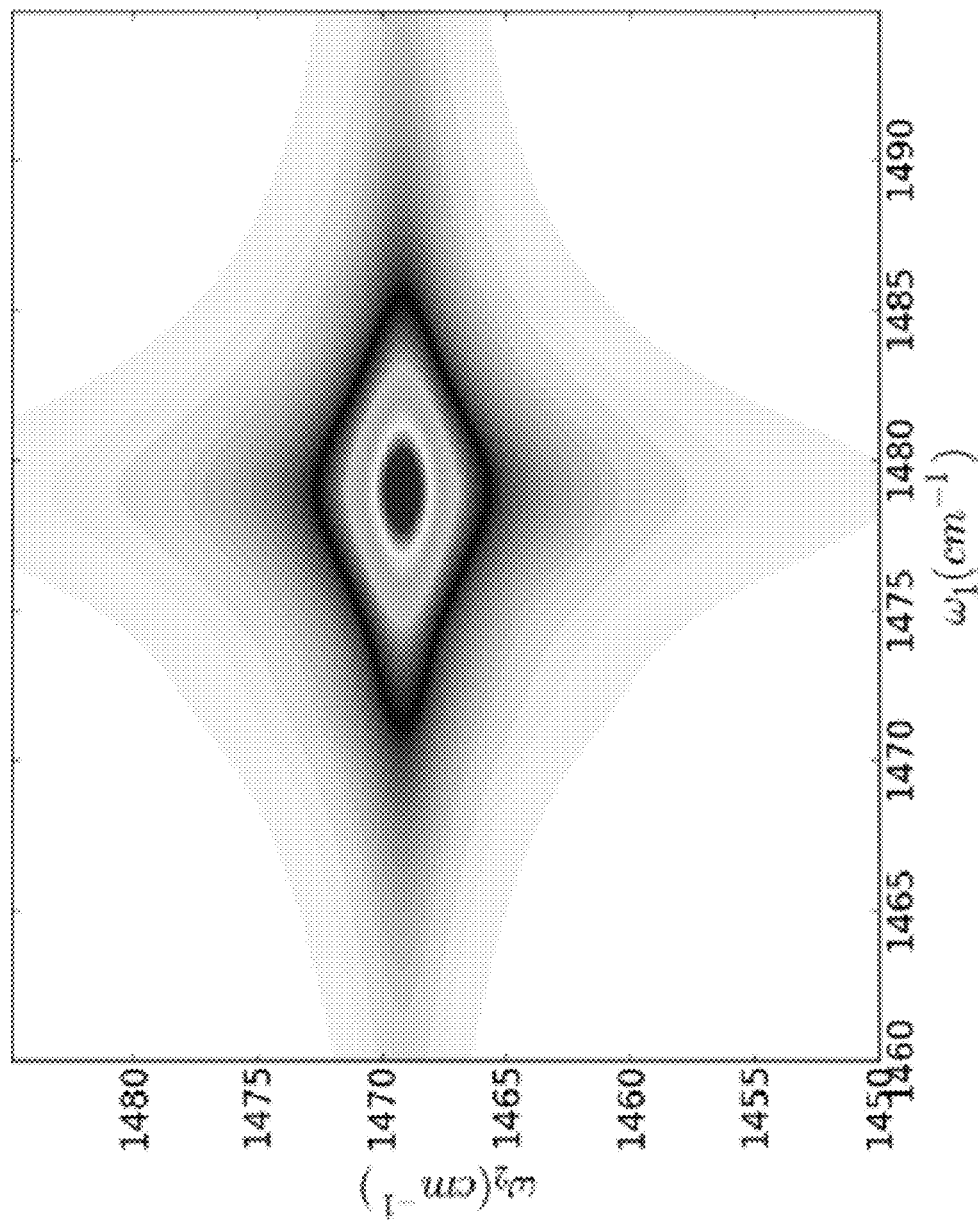
FIG. 7A shows the line shape of TSF overtone peak based solely upon $\alpha_1^* \alpha_2$ enhancements of Equation 5 without M-factor. Fundamental line shape $\alpha_1$ taken from Bertie, and excited state absorption line shape ($\alpha_2$) drawn from the Raman spectrum (FIG. 2B). (See, Bertie, J. E. John Bertie's Download Site. 2011; http://www.ualberta.ca/jbertie/JB-Download.HTM.)
Figure 7B:
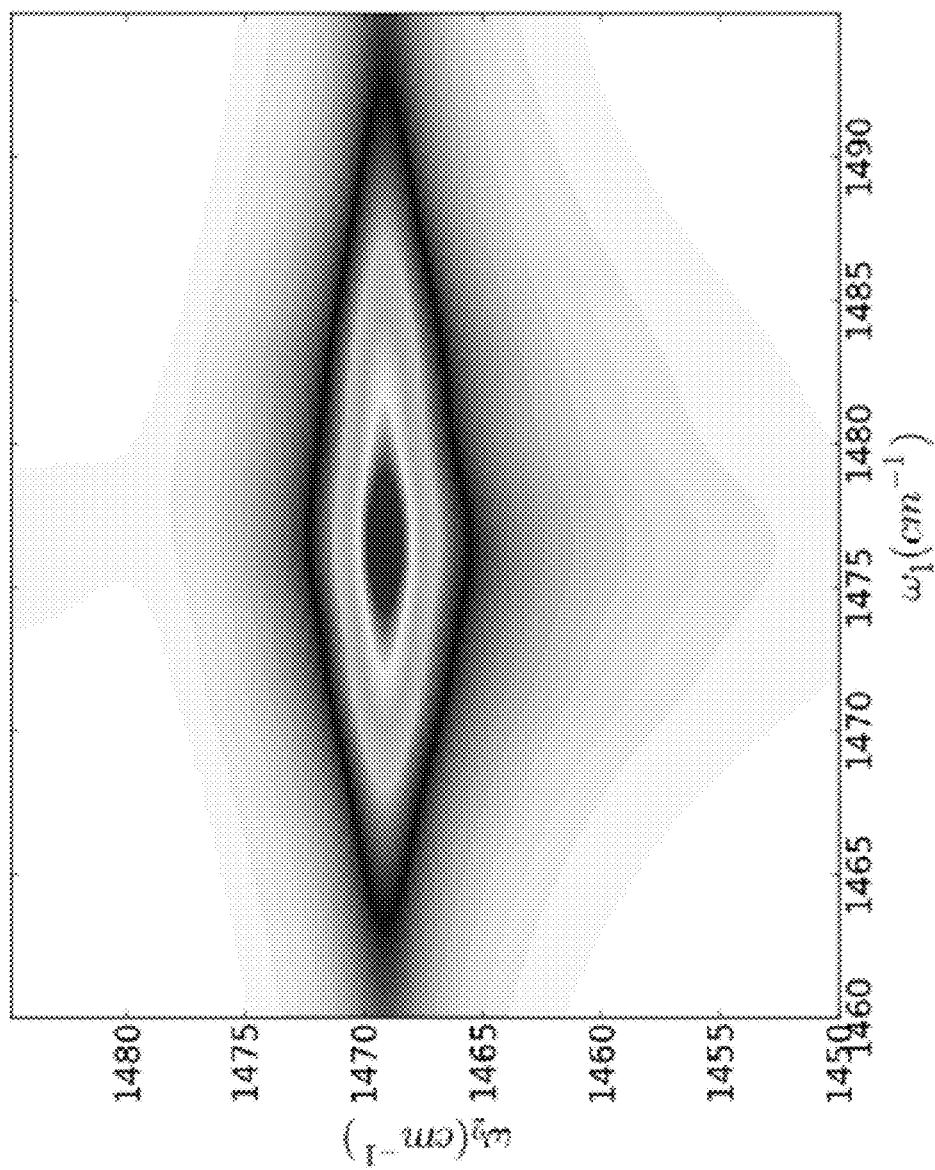
FIG. 7B shows the line shape of the TSF overtone peak incorporating M-factor at 15 μm, as well as enhancements, i.e. (Equation 6)*$\alpha_1 \alpha_2|^2$ as a representation of Equation 7. Index of refraction values provided by Bertie. (See, Bertie, J. E. John Bertie's Download Site. 2011; http://www.ualberta.ca/jbertie/JBDownload.HTM; Bertie, J. E.; Jones, R. N.; Keefe, C. D. Infrared Intensities of Liquids 0.12. Accurate Optical Constants and Molar Absorption Coefficients Between 6225 and 500 cm−1 of Benzene at 25° C., from Spectra Recorded in Several Laboratories. *Appl. Spectrosc.* 1993, 47, 891-911 and Bertie, J. E.; Lan, Z. The Refractive Index of Colorless Liquids in the Visible and Infrared—Contributions from the Absorption of Infrared and Ultraviolet Radiation and the Electronic Molar Polarizability Below 20500 cm$^{-1}$. *J. Chem. Phys.* 1995, 103, 10152-10161.)

FIG. 7A demonstrates TSF overtone peak line shape based solely upon the absorption coefficient enhancement that appears in Equation 5 with no M-factor. FIG. 7B is similar but now does take into account the M-factor (at 15 μm, with $\pm 10°$ phase-matching angles on $\omega_1$ and $\omega_2$) in addition to the enhancements.

Figure 8A:
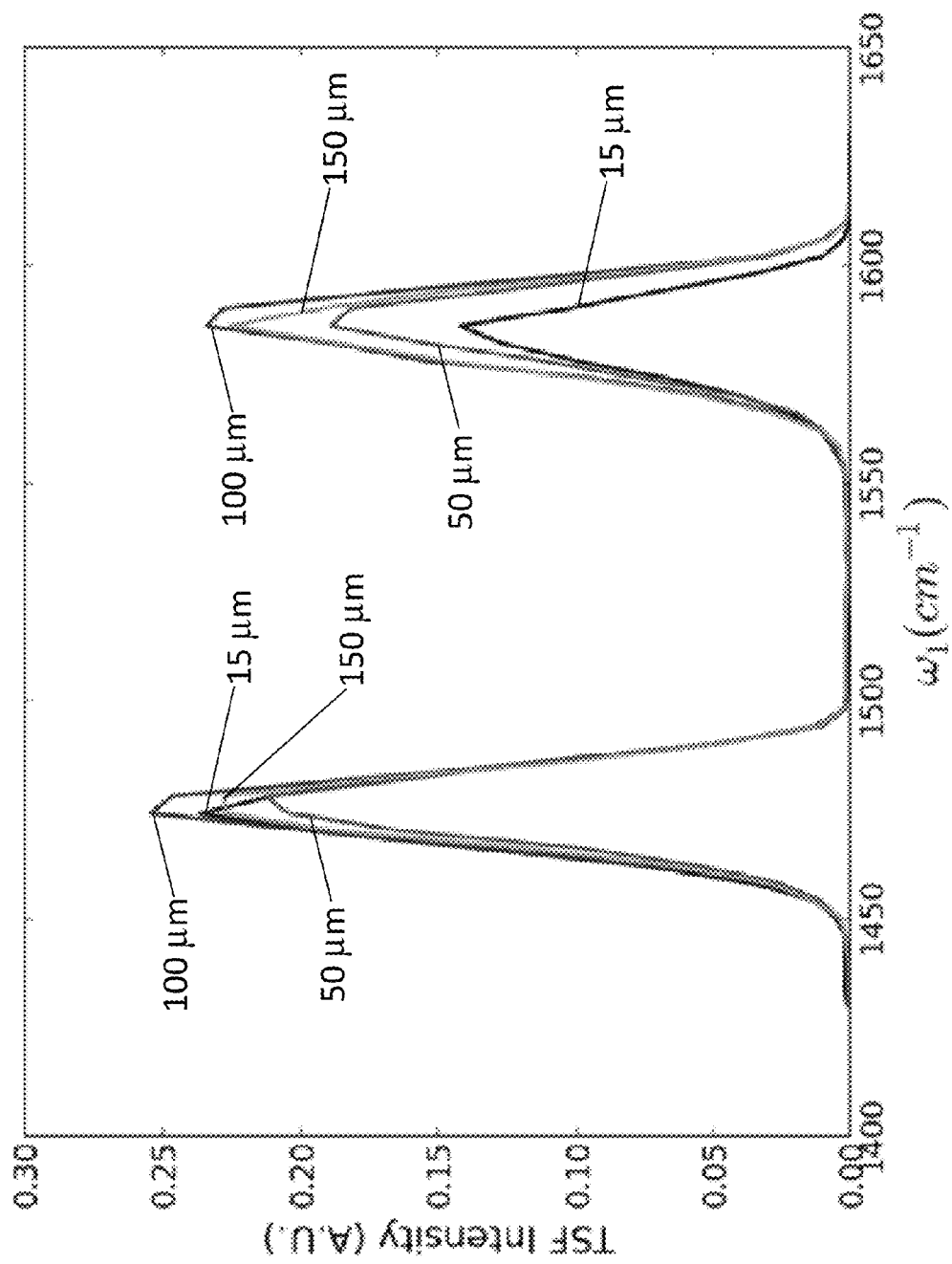
FIG. 8A shows TSF slices along $\omega_1$ were collected with $\omega_2 = 1480$ cm$^{-1}$, $\omega_m = \omega_1 + \omega_2 + \omega_3$, and $\tau_{21} = \tau_{31} = 0$ ps.
Figure 8B:
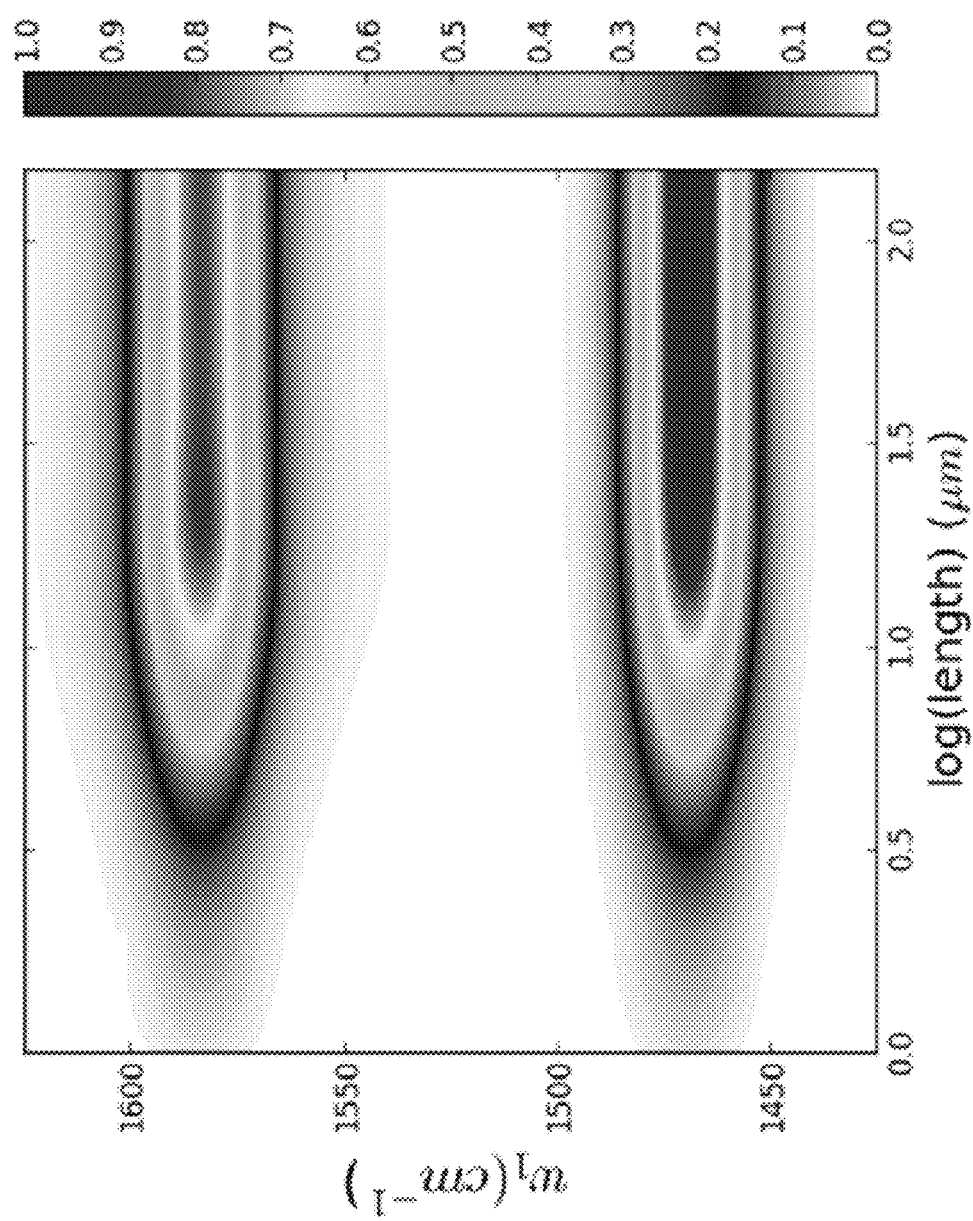
FIG. 8B shows a model of intensity as a function of path length inclusive of enhancement and M-factor. The result was convoluted along $\omega_1$ with a 20 cm$^{-1}$ Gaussian pulse to mimic experimental data.

It is also important to understand how the intrinsic phase mismatch and the absorption effects in Equation 7 together control the dependence of the TSF intensity on sample path length. FIG. 8 shows both experimental and simulated data for the path length dependence. FIG. 8A shows slices collected along $\omega_1$ with $\omega_2$ at 1480 cm$^{-1}$ and the pulses temporally overlapped. FIG. 8B uses Equation 7, the parameters summarized in Table 1, and the published molar absorptivity data to model the intensity dependence of the signal on path length. (See, Bertie, J. E. John Bertie's Download Site. 2011; http://www.ualberta.ca/jbertie/JBDownload.HTM.) The simulation predicts that the TSF intensity rises rapidly over a distance that depends on the absorption at the two excitation frequencies. The intensity becomes constant at longer path lengths where the excitation length is independent of the sample thickness and is instead defined by the attenuation of the excitation beams. The attenuation of the excitation beams shortens the path length over which the phase mismatch develops so the effects of the phase mismatch are mitigated. The simulation predicts that the initial intensity increase for the two peaks occurs over a path length of ~10 μm. For the peak at $(\omega_1, \omega_2) = (1584, 1478)$ cm$^{-1}$, the $\omega_2$ excitation beam is attenuated by the $v_{13}$ absorption while the $\omega_1$ excitation beam is not attenuated. For the peak at $(\omega_1, \omega_2) = (1470, 1478)$ cm$^{-1}$, the $\omega_2$ excitation beam is again attenuated by the $v_{13}$ absorption. The $\omega_1$ excitation beam is resonant with the overtone transition so it is shifted by the anharmonicity. The line width for this transition is sufficiently narrow and the anharmonic shift is sufficiently large that the simulation predicts the $\omega_1$ excitation beam is not appreciably attenuated. This prediction is supported by the experimental data. The peak intensity at (1470, 1478) cm$^{-1}$ does not depend on the path length. Although there are changes in the (1584, 1478) cm$^{-1}$ peak intensity with path length, the variation is not definitive.

The simulations presented in this example do not consider higher order wave mixing, preresonance enhancement from electronic states, and electronic coupling or other Fermi mixing effects.

Example 2

Triply Resonant Sum Frequency Spectroscopy of a Dye Molecule

This example is derived from Boyle et al. Triply Resonant Sum Frequency Spectroscopy: Combining Advantages of Resonance Raman and 2D-IR, submitted to *J. Phys. Chem. A* and accompanying supporting information, each which is hereby incorporated by reference in its entirety.

Introduction

Triply Resonant Sum Frequency (TRSF) spectroscopy is a fully coherent four-wave mixing technique that uses the phase matching condition $\vec{k}_s = \vec{k}_1 + \vec{k}_2 + \vec{k}_3$ where the subscripts denote the three excitation frequencies, $\omega_1$, $\omega_2$, and $\omega_3$. The subscripts do not describe the pulse time ordering since any ordering is possible. Unlike other four wave mixing methods where multiple coherence pathways interfere, defining a TRSF time ordering also defines a unique pathway. For example,

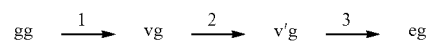

represents a unique coherence pathway where $\omega_1$ excites fundamental vibrational modes, $\omega_2$ excites overtone and combination band modes, $\omega_3$ excites the final electronic coherence, and the electronic coherence creates a cooperative and coherent resonance Raman transition returning the system to the ground state. The fundamental vibrational frequencies appear on the $\omega_1$ axis and overtones/combination bands appear on the $\omega_2$ axis. The anharmonic coupling appears as an offset from the diagonal.

In the steady state, the TRSF output coherence would be given by the density matrix element $$\rho_{eg} = \frac{\Omega_{vg} \Omega_{v'v} \Omega_{ev'}}{8 \Delta_{vg}^{(1)} \Delta_{v'g}^{(1,2)} \Delta_{eg}^{(1,2,3)}} \quad \text{Equation 13}$$

where $\Omega_{ba}$ is the Rabi frequency of the a→b transition, $\Delta_{ba}^{(i,j,k)} \equiv \omega_{ba} - \omega_1 - \omega_1 - i\Gamma_{ba}$, and $\omega_{ba}$ and $\Gamma_{ba}$ are the frequency difference and dephasing rate of the ba coherence. To gain an intuitive understanding it is possible to take advantage of the direct relationship of the resonances in this equation to absorption coefficients and Raman cross-sections. When on-resonance, the output intensity can be more simply described by the proportionality, $$I_{T(R)SF} \sim \frac{\alpha_1 \alpha_2 \sigma_{v'g} l^2 M}{\Gamma_{vg} \Gamma_{v'g}} \quad \text{Equation 14}$$

where $\alpha_i$ is the absorption coefficient of the fundamental or overtone/combination band transitions, $\sigma_{v'g}$ is the Raman cross-section of the v'g→gg transition, and l is the path length. M is a correction factor for absorption and phase matching changes.

$$M = \frac{e^{-\alpha_4 l}\left(1 - e^{\frac{\Delta\alpha l}{2}}\right) + 4e^{\frac{\Delta\alpha l}{2}} \sin^2\left(\frac{\Delta k l}{2}\right)}{\left(\frac{\Delta\alpha l}{2}\right)^2 + (\Delta k l)^2} \quad \text{Equation 15}$$

where $\alpha_i$ are the absorption coefficients at the i$^{th}$ excitation or output frequency, $\Delta\alpha = \alpha_4 - (\alpha_1 + \alpha_2 + \alpha_3)$ and $\Delta k$ is the phase mismatch of the wave vectors. For the TRSF pathway, $\Delta \vec{k} \equiv \vec{k}_1 + \vec{k}_2 + \vec{k}_3 - \vec{k}_4$ where $$k_i = \frac{n_i \omega_i}{c},$$

$n_i$ is the index of refraction of the i$^{th}$ frequency, and c is the speed of light. Equation 15 predicts a decrease in signal as the output $k_4$ is absorbed, and saturation of nonlinear gain at the path length where inputs $k_1$, $k_2$, and $k_3$ have been absorbed.

In the limit of negligible absorption, the M factor reduces to the familiar $\text{sinc}^2(kl/2)$ dependence. The TRSF pathway cannot be phase matched in systems with normal dispersion since the indices of refraction make the $\vec{k}_4$ output wave vector larger than the $\vec{k}_1 + \vec{k}_2 + \vec{k}_3$ nonlinear polarization that creates it. Consequently, until the present application it hasn't been used for CMDS experiments. Unexpectedly, the inventors have observed high output intensities. The inventors have determined the high output intensity can be explained at least in part, because the three resonance enhancements are multiplicative and create a high nonlinear gain over a path length shorter than the inverse of their phase-mismatch, $\Delta k$. This gain (Equation 14) relies upon the brightness of coupled infrared modes ($\alpha_1$, $\alpha_2$) and the Raman cross-section of the resulting overtone or combination band ($\sigma$). The high gain reduces the effects of absorption and phase mismatch so they do not play a role in these experiments.

As discussed below, TRSF is demonstrated on the donor-acceptor styryl ionic dye 2-(6-(p-dimethylaminophenyl)-2,4-neopentylene-1,3,5-hexatrienyl)-3-ethylbenzothiazolium perchlorate), or Styryl 9M.

Experimental.

The CMDS experimental system used a 1 kHz Ti:Sapphire regenerative amplifier to pump two independently tunable optical parametric amplifiers to create infrared frequencies $\omega_1$ and $\omega_2$. Residual pump light from one OPA provided the $\omega_3$ pulse. The three pulses were focused into the sample using a linear phase matching geometry where $\omega_1$ and $\omega_2$ were displaced $\pm 10°$ from a central $\omega_3$ pulse, and the $\omega_4$ output was collinear with $\omega_3$. The focal region had a spot size <100 μm. The $\omega_1$ and $\omega_2$ frequencies were independently scanned over the 1250-1700 cm$^{-1}$ range with $\omega_3$=800 nm. Residual $\omega_3$ light was removed by a holographic filter stack as well as a monochromator which resolved the $\omega_4$ frequency with a resolution of ~100 cm$^{-1}$. A photomultiplier measured the TRSF output signal over the 628-668 nm wavelength range. These frequencies are resonant with the red side of the Styryl 9M electronic transition.

The spectral and temporal pulse widths were ~15 cm$^{-1}$ and ~1.2 ps FWHM for the $\omega_1$ pulse and ~18 cm$^{-1}$ and ~1.0 ps FWHM for the $\omega_2$ pulse. The pulse energies were ~0.5-1 μJ/pulse. The $\omega_3$ pulse was ~2 ps FWHM and pulse energies between 0.5 and 5 mW. Scanning $\omega_1$ and $\omega_2$ and measuring the output beam intensity creates two dimensional spectra while scanning the time delays between the pulses measures the coherent dynamics. Two dimensional Wigner plots of the frequency and time delay show the state resolved dynamics. The excitation pulse time delays were changed during spectral scans to correct for the spectral dependence of the pulse timing. This correction ensured the time delays between pulses remained constant.

Figure 15:
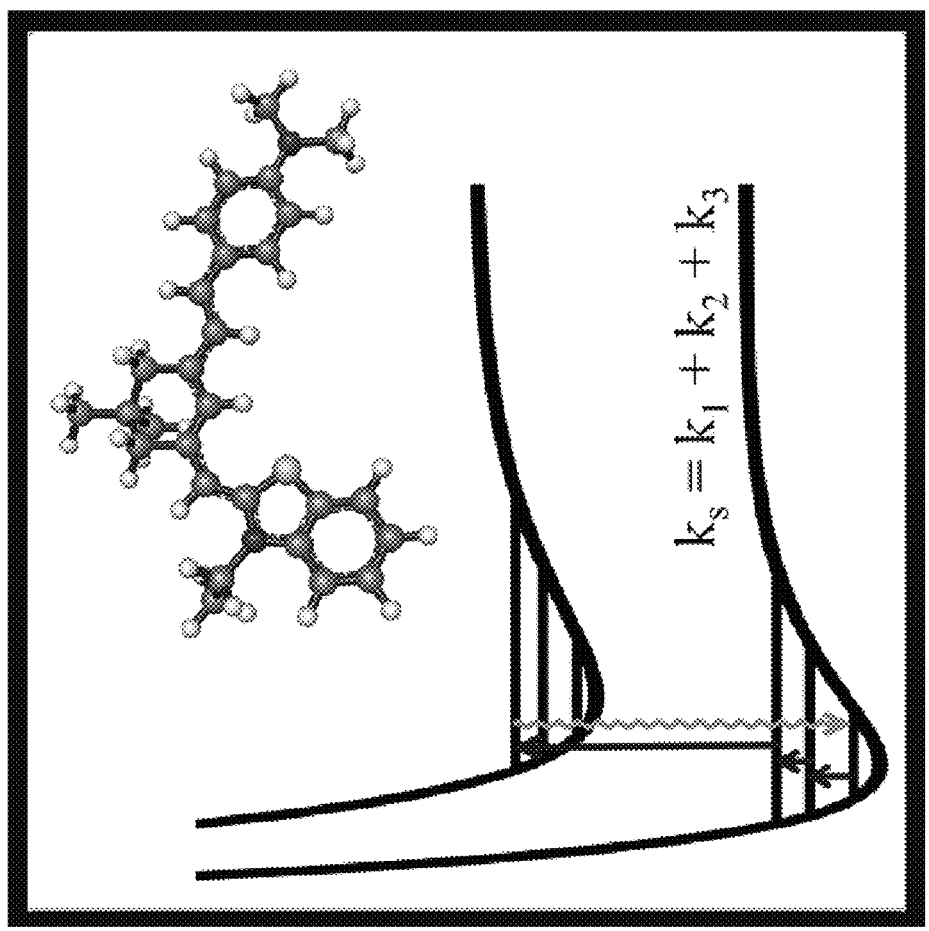
FIG. 15 depicts a schematic of a TRSF spectroscopic analysis of Styryl 9M according to an illustrative embodiment.

Styryl 9M was obtained as LDS821 from Exciton. A schematic of the TRSF excitation scheme is shown in FIG. 15.

Results/Discussion

FTIR absorption spectra of a high concentration Styryl 9M solution with the solvent contribution removed (3 mM Styryl 9M, 200 μm path length) and the low concentration sample used for the TRSF spectrum (300 μM Styryl 9M with 180 mM benzene in DACN solution, 25 μm path length) were obtained. The latter sample included benzene at $100x$ higher concentration than Styryl 9M in order to compare molecules with and without resonant electronic states. It also had a shorter path length, which together with the lower concentration made the dye absorbance 80 times smaller. Since the representative Styryl 9M 1430 cm$^{-1}$ mode has a molar absorptivity of ~830 M$^{-1}$ cm$^{-1}$, its absorbance would be <0.001 in the TRSF sample. The benzene line observed at 1480 cm$^{-1}$ has an optical density of ~0.04 and a molar absorptivity of 110 M$^{-1}$ cm$^{-1}$. The broad 1370 cm$^{-1}$ peak observed is the deuterated acetonitrile solvent (DACN).

A resonance Raman spectrum of Styryl 9M in DACN excited at 514 nm was also obtained. The resonance Raman spectrum of the dye contains the same modes observed in FTIR although the intensities differ. An exception is that the brightest peak appears at 1522 cm$^{-1}$ in the FTIR and at 1532 cm$^{-1}$ in the resonance Raman spectrum. Neither feature is Lorentzian and both fit well to separate modes at 1521 and 1534 cm$^{-1}$. A UV/Visible spectrum of 300 μM Styryl 9M with 180 mM benzene in DACN solution, 25 μm path length was also obtained. The Styryl 9M visible absorption spectrum peaks at 565 nm, with a FWHM of 132 nm, and $\epsilon=7\times10^4$ M$^{-1}$ cm$^{-1}$.

Figure 11:
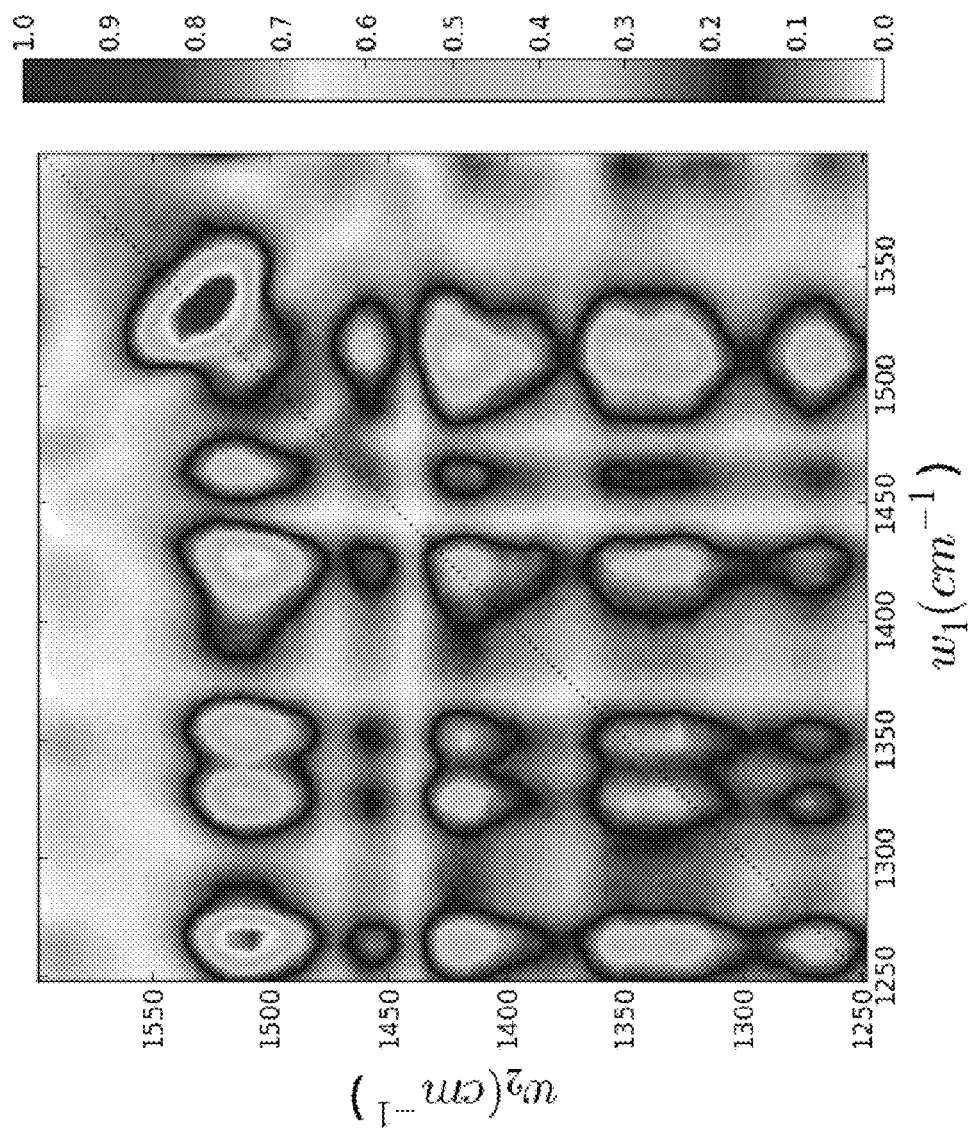
FIG. 11 shows a triply resonant sum frequency (TRSF) spectrum of 300 μM Styryl 9M with 180 mM benzene in DACN solution, 25 μm path length. $\tau_{12} = 0$ ps, $\tau_{32} = 2.5$ ps.

FIG. 11 shows the TRSF spectrum of 300 μM Styryl 9M, 180 mM benzene in DACN solution and 25 μm path length, obtained with $\omega_1$ and $\omega_2$ temporally overlapped and $\omega_3$ delayed 2.5 ps. The $\omega_3$ power used in this scan was ~2 mW. This time ordering should create a symmetric spectrum since each field can cause the first or second interaction. Asymmetries in peak width and intensity are due to asymmetries in the exciting fields. All major vibrational modes seen in the Raman and FTIR spectra appear in the 2D TRSF spectrum, both as diagonal peaks where the interactions involve the fundamental and overtone transitions and as cross peaks where the interactions involve the fundamental and combination band transitions. Cross peaks appear between all modes except for one feature at ~1530 cm$^{-1}$ which notably does not display observable coupling to any other modes. Monochromator scans show the output frequency appears at $\omega_4=\omega_1+\omega_2+\omega_3$ with the ~25 cm$^{-1}$ width of the excitation pulses. There is no detectable fluorescence.

A broad background at 1370 cm$^{-1}$ due to DACN is absent in the TRSF spectrum, and in fact no DACN peaks could be observed in nearby spectral ranges when scanning just solvent. The 1480 cm$^{-1}$ diagonal peak of benzene is also absent in FIG. 11 despite having an optical density ~50 times higher. This peak can be observed with higher $\omega_3$ pulse powers in samples without the dye. Similarly, a water impurity has absorbance ~0.1 at 1650 cm$^{-1}$ that also appears at higher pulse powers or longer path lengths. These observations support the fact that electronic resonance enhancement allows detection of vibrational couplings that cannot be seen by infrared absorption or 2D-IR.

The TRSF spectrum of Styryl 9M is quite rich. This dye is extensively conjugated and the vibrational modes are delocalized. Previous experiments show that excitation to the excited electronic state causes reorganization to a Locally Excited (LE) state in <1 ps and to a Twisted Intramolecular Charge Transfer (TICT) state in ~4 ps. Though TRSF does not follow the excited electronic state evolution, the presence of the cross peaks shows that the electronic potential energy surface changes along the different normal mode coordinates. In Triple Sum Frequency (TSF) experiments without electronic resonances, the overtones and combination bands appear because of their Fermi resonance with Raman-active fundamental modes. These transitions dominate TSF spectra since Raman overtone and combination bands are weak.

Figures 12A, 12B:
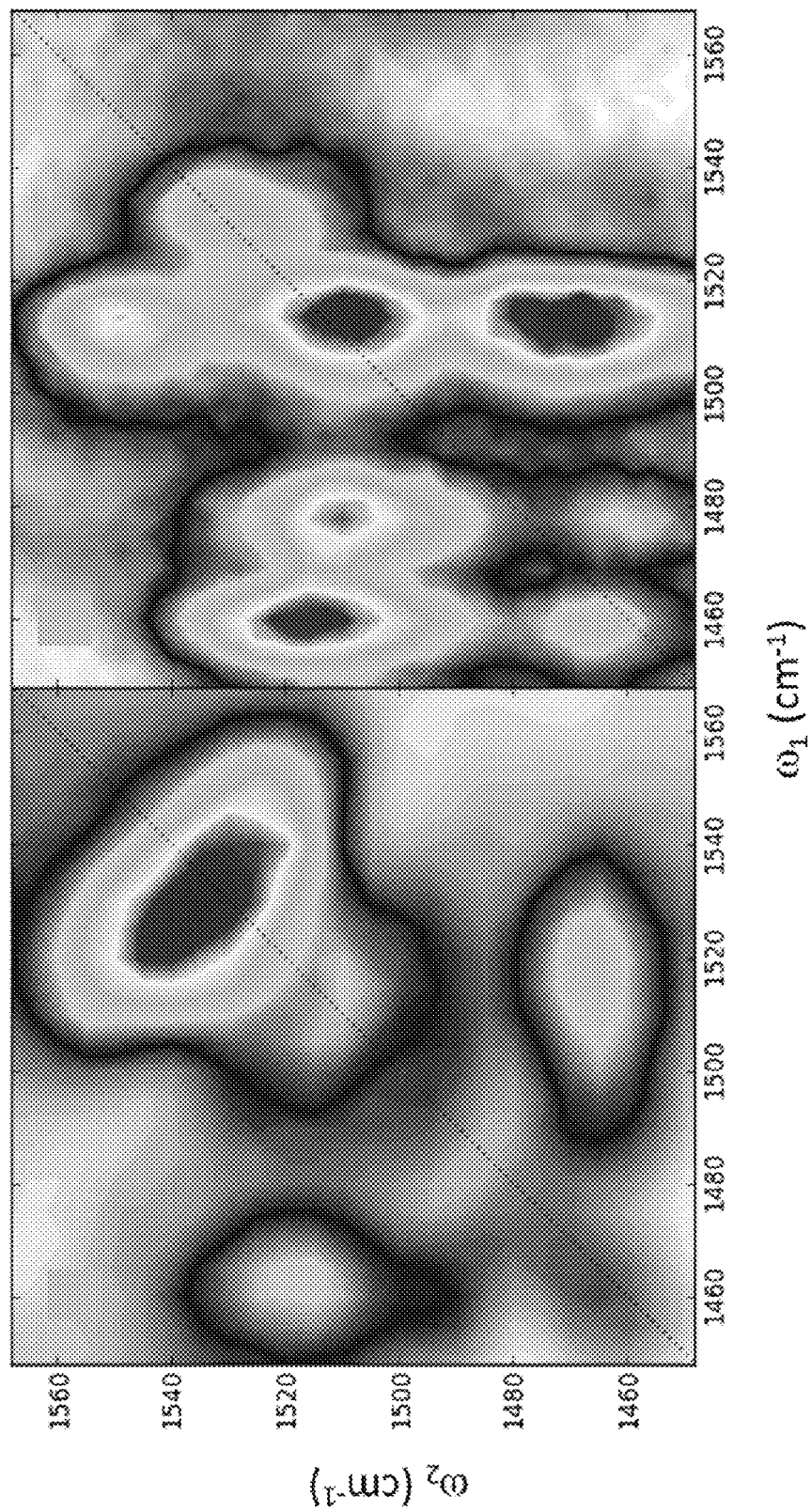
FIG. 12A shows the TRSF spectrum of 300 μM Styryl 9M with 180 mM benzene in DACN solution, 25 μm path length. $\tau_{21} = 0$ ps, $\tau_{32} = 2.5$ ps (taken from FIG. 11).
FIG. 12B shows the TRSF spectrum of 2 mM Styryl 9M in DACN solution, 25 μm path length. $\tau_{21} = 1.75$ ps and $\tau_{32} = 2$ ps.

The spectrum changes when the excitation pulses are not temporally overlapped. FIG. 12A-B compares the spectral changes in a section of FIG. 11 when the time delays are $\tau_{21}=1.75$ ps and $\tau_{32}=2$ ps. Here $\omega_1$ first excites the fundamental modes and then $\omega_2$ excites the combinations bands and overtones. Anharmonic shifts now appear as the frequency difference of the peaks on the $\omega_2$ axis relative to their frequency on the $\omega_1$ axis. A two-dimensional Gaussian fit of individual peaks in FIG. 12B gives the peak positions and the resulting anharmonicities (Table 2). The anharmonicities are smaller than those seen in typical CMDS spectra and demonstrate the ability of the TRSF pathway to examine peaks with vanishingly small mechanical anharmonicity. The small anharmonicities would create very weak 2D-IR features because of the destructive interference between coherence pathways.

TABLE 2

Peak frequency maxima of FIG. 12B fit to a 2D gaussian function. This data was also collected reversing the roles of the two OPAs and the difference was taken as an estimate of experimental error. On the $\omega_1$ axis, error $\approx 1$ cm$^{-1}$; on the $\omega_2$ axis error $\approx 2$ cm$^{-1}$.

| $\omega_1$ (cm$^{-1}$) | $\omega_2$ (cm$^{-1}$) | anharmonicity of $\omega_2$ (cm$^{-1}$) |
|---|---|---|
| 1531.1 | 1526.5 | −4.6 |
| 1511.6 | 1510.3 | −1.3 |
| 1477.1 | 1509.0 | −2.6 |
| 1459.1 | 1513.6 | +2.0 |

Two types of features are left out of Table 2. The first is the prominent antidiagonal mode appearing at ~1530 cm$^{-1}$ in FIG. 12A. The antidiagonal shape suggests a $\Delta_{v'g}^{1,2}=\omega_{v'g}-\omega_1-\omega_2-i\Gamma_{v'g}$ factor in Equation 13, where $\omega_{v'g}$~3060 cm$^{-1}$. In FIG. 12B this feature resolves into two peaks: $(\omega_1, \omega_2)=(1512,1545)$ cm$^{-1}$ and $(\omega_1, \omega_2)=(1531,1527)$ cm$^{-1}$. This observation is curious for two reasons. One is the lack of cross-mode coupling on the 1530 cm$^{-1}$ peak, and the other is the asymmetry of the (1512,1545) cm$^{-1}$ peak. All other cross peaks appear on both sides of the diagonal because each excitation beam can excite the fundamental or overtone/combination band transition. This asymmetry was also observed in non-electronically resonant TSF of benzene. In that study, the Fermi resonance of the C=C ring breathing mode overtone and the C—H stretch fundamental resulted in two mixed modes. Each mode had overtone character and so each could be accessed in excited state absorption from the C=C fundamental. For benzene, this Fermi resonance resulted in one "diagonal" peak at $(\omega_1, \omega_2)$ ~(1480,1480) cm$^{-1}$ and one "cross peak" at ~(1480,1580) cm$^{-1}$, the sum of which reach the (primarily) $A_{1g}$ C—H stretch mode at ~3060 cm$^{-1}$. With $\tau_{21}>1$ ps, no peak appeared at (1580,1480) cm$^{-1}$ because there was no fundamental mode at 1580 cm$^{-1}$.

It is therefore proposed that the (1512,1545) cm$^{-1}$ peak is also caused by a Fermi resonance. This idea requires a fundamental mode at the sum frequency, 3057 cm$^{-1}$. The Raman and solvated IR spectra do not provide guidance since it was not possible to detect any modes in the region surrounding this frequency of the Raman spectrum due to fluorescence, and the FTIR of the solvated Styryl 9M C—H modes are obscured by solvent absorption. Attenuated total reflectance (ATR) IR shows overlapping peaks at ~3064/3072 cm$^{-1}$ but these can be expected to shift in solvent. The 3057 cm$^{-1}$ sum frequency is also consistent with that of the diagonal peak in FIG. 12B at (1531,1527) cm$^{-1}$, and with the entire antidiagonal feature in FIG. 12A. The 1512 cm$^{-1}$ mode is buried in the FTIR and Raman spectra but becomes significant in TRSF. Since infrared pulses are temporally overlapped in FIG. 12A, they can excite a two photon transition to the Fermi resonance state where either $\omega_1$ or $\omega_2$ are resonant with the 1512 or 1530 cm$^{-1}$ fundamentals. A time delay between the infrared pulses defines the time ordering, reduces the number of pathways, and resolves the antidiagonal feature into the (1531,1527) cm$^{-1}$ diagonal and the Fermi cross peak at (1512,1545) cm$^{-1}$. This 1531 cm$^{-1}$ has no observable coupling to other modes in this region. It may be that this mode has different character than the ring modes representing the other features in the spectrum.

The second feature is the pair of peaks appearing at $(\omega_1, \omega_2)=(1459,1468)$ and (1477,1463) cm$^{-1}$ in FIG. 12B. Only one detectable resonance appears at 1467 cm$^{-1}$ in this region of FIG. 12A. In the FTIR and resonance Raman spectra, two resonances clearly appeared at 1464.3 and 1473.3 cm$^{-1}$. Since this splitting is within the bandwidth of the laser pulses used, they would not be resolved in the spectra. The two peaks in FIG. 12B are attributed to the frequency domain analogue of quantum beating. It has been previously observed that the quantum beating between two unresolved states appears as a periodic splitting and collapse of the unresolved peaks. The 9 cm$^{-1}$ splitting seen in the FTIR and Raman spectra would create frequency domain quantum beating with a 3.7 ps period.

Figure 13:
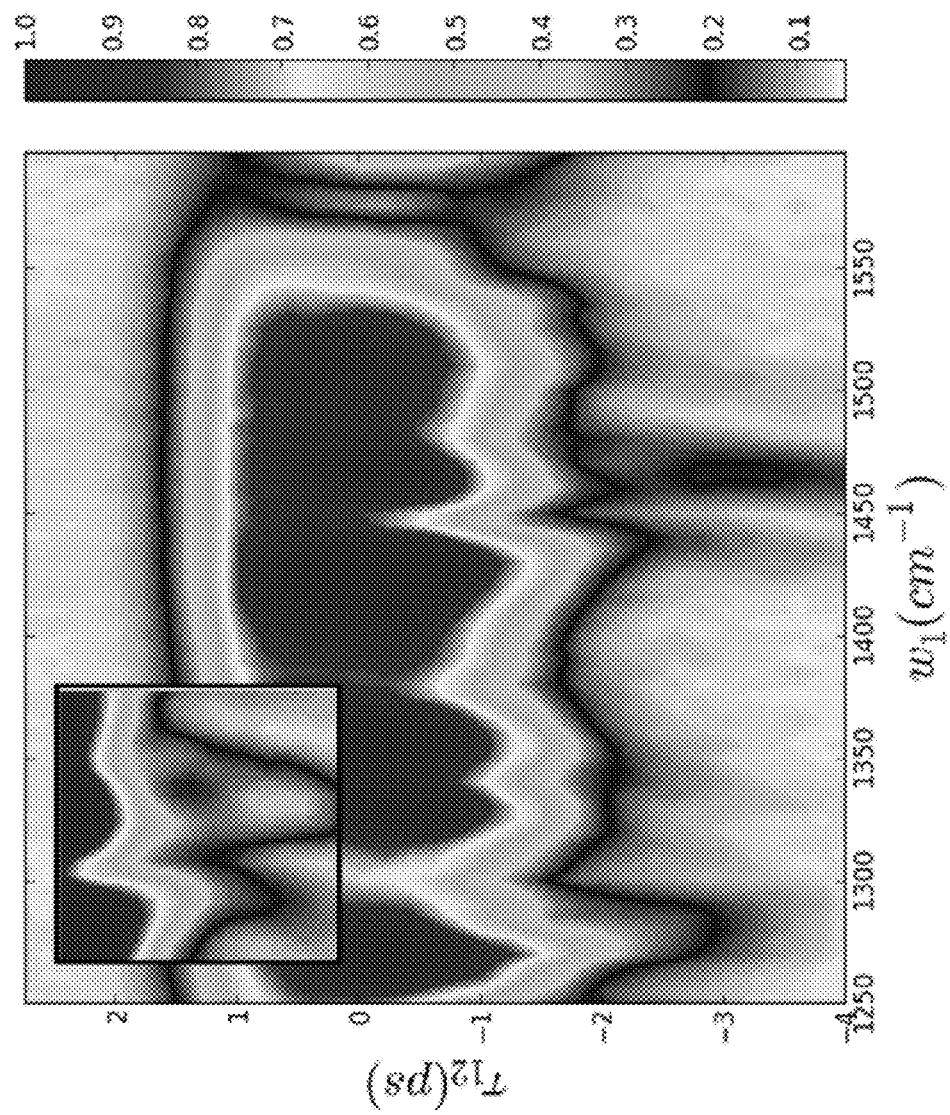
FIG. 13 shows a Wigner scan of 2 mM Styryl 9M with $\omega_2 = 1510$ cm$^{-1}$, $\tau_{32} = 0$ ps, $\omega_3$ power ~1 mW. The inset shows the 1418-1500 cm$^{-1}$, −3.5 to −0.5 ps, region of Wigner scan with the same conditions except $\tau_{32} = 2$ ps, $\omega_3$ power ~4 mW. Vertical slices at <1310 cm$^{-1}$ had $\tau_{12}$ values shifted up 0-0.5 ps to correct for inaccuracies in delay calibration in this region. Each spectrum is plotted on the amplitude level, $\sqrt{\text{Int}}$.

In order to measure the dynamics and provide further evidence for spectral quantum beating, a Wigner scan was collected where $\omega_2$ was fixed at 1510 cm$^{-1}$, $\tau_{32}$ was fixed at 0 ps, and $\omega_1$ was scanned as a function of $\tau_{12}$ (FIG. 13). When $\tau_{12}$ is positive, the $\omega_1$ pulse arrives after the $\omega_2$ and $\omega_3$ pulses. Since the vibronic coherence created by the first two pulses dephases quickly, the coherent output decays rapidly at short $\tau_{12}$ times. When $\tau_{12}$ is negative, the dynamics of all the combination bands with the 1510 cm$^{-1}$ mode are observed. The quantum beating of the 1464 and 1473 cm$^{-1}$ modes in FIG. 4 is also seen here. When all pulses are overlapped at $\tau_{12}=0$, these two modes are not resolved, but when $\omega_1$ arrives 2 ps prior to $\omega_2$ and $\omega_3$, a gap develops between the two. At $\tau_{12}$~−3.3 ps that gap has disappeared again, verifying the splitting frequency and therefore the origin of the beating behavior. This splitting is shown more distinctly in the inset, which was collected with the same parameters except $\tau_{32}$ was fixed at 2 ps and greater $\omega_3$ power was used. Quantum beating allows mixed-domain spectroscopy to effectively resolve peaks within the pulse bandwidth in a completely analogous manner to time domain spectroscopy.

The detection limit in this example was defined by competition with nonresonant background. The line-shape changes between high and low concentrations were examined. The line shape becomes more dispersive as the nonresonant background begins to dominate at low concentrations. In the examination, traces of a diagonal cross-section of the TRSF spectrum in FIG. 11 and traces of the same cross-section when the Styryl 9M concentration is 50 µM (i.e. ~0.15 mOD in the infrared) were compared to simulations of $|\chi^{(3)}|^2$ spectra with a constant nonresonant background, $\chi_{NR}^{(3)}$, from the solvent. It was assumed that the frequency dependence can be modeled using a steady state approximation for the two vibrational resonances:

$$\chi^{(3)}(\omega_1, \omega_2) = \chi_{NR} + \sum_j \sum_k N \frac{\mu_j \mu_j \mu_3 \mu_4}{(\delta_{j1} - i\Gamma_j)(\delta_{k2} - i\Gamma_k)} \quad \text{Equation 16}$$

where j and k are the 17 most important vibrational states, $\mu_{jk}$~$\sqrt{A_{jk}\Gamma_{jk}}$, A is the area of a Lorentzian, $\Gamma$ is its dephasing rate, $\delta_{jn}=\omega_j-\omega_n$, $\omega_n$ is the frequency of the light field, and $\chi_{NR}=e^{i\theta}$ (represented as constant across the region and with constant $\theta$ assumed between high and low concentration). The best match to the data corresponded to $\theta=35°$. The agreement shows that the line-shape changes are caused by coherent interference between the resonant and nonresonant contributions to $\chi^{(3)}$. It has been demonstrated how this model can be used to extract the absolute values of the real and imaginary parts of $\chi^{(3)}$ from the dispersive line shapes. The heterodyning from the nonresonant background therefore represents an extension of the method's detection limits to very low concentrations.

Conclusions

The electronic resonance in the TRSF pathway provides strong multidimensional vibrational spectra of the Styryl 9M dye, despite optical densities <0.001 in the infrared. The pathway uses two infrared pulses to first excite fundamental and overtone/combination band vibrational modes, then induces a two-quantum Raman transition using a visible pulse to generate coherent output. Species resonant with this third interaction gain significant resonant enhancement above the background due to the huge transition dipole moments of electronic states. This allowed detection of 50 μM Styryl 9M (or ~0.1 mOD in the infrared), discrimination against strong solvent and cosolute absorption, and multidimensional vibrational spectroscopy of modes with small anharmonicity.

The displacement of the excited state potential energy surface along multiple normal mode coordinates provides the coupling required for observing cross-peaks in the 2D spectra. Earlier TSF experiments without the electronic resonance used Fermi resonances with Raman active fundamental modes to create the overtone and combination band transitions in the 2D spectra. Not only does the electronic resonance provide the coupling required to see multiple modes, it also provides a powerful way to correlate the coupled electronic and vibrational states. Because TRSF has only coherence pathway, coupled modes can be observed without the need for mechanical anharmonicity that is required for 2D-IR or TRIVE experiments. Time delays between the first and second infrared interactions resolves the fundamental and overtone/combination bands onto orthogonal axes (FIG. 12) so the mechanical anharmonicity appears as the peak offset from the diagonal in the 2D spectra. This attribute allowed measurement of anharmonicities of order ~2 cm$^{-1}$ for Styryl 9M (Table 2), free of the pathway interference that makes such determinations more difficult in 2D-IR and TRIVE. Coherent dynamics and quantum beating can also be observed in TRSF, as demonstrated in the Wigner plot in FIG. 13.

Observation of coupling between vibrational and electronic states in this technique is complementary to other nonlinear spectroscopies such as full resonant Doubly Vibrationally Enhanced Four-Wave Mixing (DOVE-FWM) and Coherent Anti-Stokes Raman Scattering (CARS). DOVE and T(R)SF experiments are similar because they both probe coupling between two vibrational resonances and one electronic and both are done as mixed-domain spectroscopy. However, DOVE employs the phase-matching criterion $k_s=k_1-k_2+k_3$, where $k_1$ and $k_2$ are infrared fields and $k_3$ is visible or ultraviolet. The $k_2$ frequency matches a fundamental vibrational mode and the $k_1$ an overtone or combination band frequency. Because these vibrations are excited with opposite phase, the visible excitation results in a single quantum Raman transition between the two vibrational modes. In the two DOVE-IR pathways, the $k_1$ and $k_2$ beams both cause absorptive transitions from the ground state to vibrational modes with ungerade character. In the DOVE-Raman pathway, the $k_1$ beam and the $k_2$ beams excite a Raman transition where the $k_1$ beam excites an ungerade overtone/combination band state and the $k_2$ beam stimulates emission to the gerade fundamental vibrational mode. Fully resonant CARS experiments involve resonance with two electronic states and a vibrational state. Both electronic resonances involve ungerade electronic states while the vibrational resonance involves a gerade vibrational state. In contrast, the first interaction in T(R)SF excites states with ungerade fundamental character and the second interaction excites gerade overtone/combination band states, similar to 2D-IR or TRIVE.

The electronic enhancement of TRSF spectroscopy is dependent on the molar absorptivity of the electronic transition and the displacement of the electronic potential energy surface along the normal mode coordinates. These transitions are much stronger than vibrational transitions and greatly enhance the detection limits of CMDS methods. The Styryl 9M dye used in this example has an absorptivity, $\epsilon=7\times10^4$ M$^{-1}$cm$^{-1}$, that is typical of electronic resonances in other organic molecules, metalloproteins, catalysts, etc. This methodology should therefore be a widely applicable technique for obtaining multidimensional vibrational and electronic spectra at low concentration while also suppressing nonresonant solvent and cosolutes background processes.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," and the like includes the number recited and refers to ranges which can be subsequently broken down into subranges as discussed above. Finally, as will be understood by one skilled in the art, a range includes each individual member.

The foregoing description of illustrative embodiments of the disclosed subject matter has been presented for purposes of illustration and of description. It is not intended to be exhaustive or to limit the disclosed subject matter to the precise form disclosed, and modifications and variations are possible in light of the above teachings or may be acquired from practice of the disclosed subject matter. The embodiments were chosen and described in order to explain the principles of the disclosed subject matter and as practical applications of the disclosed subject matter to enable one skilled in the art to utilize the disclosed subject matter in various embodiments and with various modifications as suited to the particular use contemplated. It is intended that the scope of the disclosed subject matter be defined by the claims appended hereto and their equivalents.

What is claimed is:

1. A method of obtaining a multidimensional image of a sample, the method comprising:
   (a) directing a first coherent light pulse having a first frequency $\omega_1$ and a first wave vector $k_1$ at a first location in a sample,
   (b) directing a second coherent light pulse having a second frequency $\omega_2$ and a second wave vector $k_2$ at the first location,
   (c) directing a third coherent light pulse having a third frequency $\omega_3$ and a third wave vector $k_3$ at the first location and (d) detecting a coherent output signal having a fourth frequency $\omega_4$ and a fourth wave vector $k_4$ from the first location, wherein $\omega_4 = \pm\omega_1 \pm\omega_2 \pm\omega_3$ and $k_4 = \pm k_1 \pm k_2 \pm k_3$, wherein at least two of the coherent light pulses each are configured to excite a different transition to a discrete quantum state of a molecule or molecular functionality in the sample, and further wherein steps (a)-(d) are repeated at a sufficient number of other locations in the sample to provide the multidimensional image.

2. The method of claim 1, wherein $\omega_4 = \omega_1 + \omega_2 + \omega_3$ and $k_4 = k_1 + k_2 + k_3$.

3. The method of claim 2, wherein the three coherent light pulses are each configured to excite a different transition to a discrete quantum state in the molecule or molecular functionality.

4. The method of claim 2, wherein one of the coherent light pulses is configured to excite a transition to a vibrational quantum state, one of the coherent light pulses is configured to excite a transition to a different vibrational quantum state and one of the coherent light pulses is configured to excite a transition to a virtual electronic state, whereby a Raman transition is induced returning the molecule or molecular functionality to a lower energy state.

5. The method of claim 2, wherein one of the coherent light pulses is configured to excite a transition to a vibrational quantum state, one of the coherent light pulses is configured to excite a transition to an electronic quantum state and one of the coherent light pulses is configured to excite a transition to a virtual electronic state, whereby a Raman transition is induced returning the molecule or molecular functionality to a lower energy state.

6. The method of claim 3, wherein one of the coherent light pulses is configured to excite a transition to a vibrational quantum state, one of the coherent light pulses is configured to excite a transition to a different vibrational quantum state and one of the coherent light pulses is configured to excite a transition to an electronic quantum state, whereby a resonance Raman transition is induced returning the molecule or molecular functionality to a lower energy state.

7. The method of claim 3, wherein one of the coherent light pulses is configured to excite a transition to a vibrational quantum state, one of the coherent light pulses is configured to excite a transition to an electronic quantum state and one of the coherent light pulses is configured to excite a transition to a different electronic quantum state, whereby a resonance Raman transition is induced returning the molecule or molecular functionality to a lower energy state.

8. The method of claim 2, wherein the frequencies of the at least two coherent light pulses are resonant with their respective transitions.

9. The method of claim 3, wherein the frequencies of the three coherent light pulses are resonant with their respective transitions.

10. The method of claim 2, wherein the three coherent light pulses interact with the sample to generate the coherent output signal over a path length and the path length is in the range of from about 1 μm to about 200 μm.

11. The method of claim 2, wherein the multidimensional image is a three-dimensional image.

12. The method of claim 2, wherein at least two of the coherent light pulses are independently tunable.

13. The method of claim 2, wherein the three coherent light pulses are independently tunable.

14. The method of claim 2, wherein the three coherent light pulses are configured in a non-collinear beam geometry.

15. A scanning microscope for obtaining a multidimensional image of a sample, the scanning microscope comprising:

(a) optics configured to receive coherent light pulses and to direct the coherent light pulses to a first location in the sample, the coherent light pulses comprising:

(i) a first coherent light pulse having a first frequency $\omega_1$ and a first wave vector $k_1$, (ii) a second coherent light pulse having a second frequency $\omega_2$ and a second wave vector $k_2$, and (iii) a third coherent light pulse having a third frequency $\omega_3$ and a third wave vector $k_3$, wherein at least two of the coherent light pulses each are configured to excite a different transition to a discrete quantum state of a molecule or molecular functionality in the sample;

(b) a stage configured to support the sample; and (c) a detector positioned to detect a coherent output signal generated from the first location, the coherent output signal having a fourth frequency $\omega_4$ and a fourth wave vector $k_4$, wherein $\omega_4 = \pm\omega_1 \pm\omega_2 \pm\omega_3$ and $k_4 = \pm k_1 \pm k_2 \pm k_3$, and further wherein the scanning microscope is configured to illuminate a sufficient number of other locations in the sample with the three coherent light pulses to provide the multidimensional image.

16. The scanning microscope of claim 15, wherein $\omega_4 = \omega_1 + \omega_2 + \omega_3$ and $k_4 = k_1 + k_2 + k_3$.

17. The scanning microscope of claim 16, wherein the optics are configured to direct the three coherent light pulses in a non-collinear beam geometry.

18. The scanning microscope of claim 16, further comprising one or more light sources configured to generate the three coherent light pulses.

19. The scanning microscope of claim 18, wherein at least two of the coherent light pulses are independently tunable.

20. The scanning microscope of claim 18, wherein the three coherent light pulses are independently tunable.

* * * * *